(12) United States Patent
Martin et al.

(10) Patent No.: US 7,482,012 B2
(45) Date of Patent: Jan. 27, 2009

(54) STREPTOCOCCUS PYOGENES POLYPEPTIDES AND CORRESPONDING DNA FRAGMENTS

(75) Inventors: Denis Martin, St-Augustin-de-Desmaures (CA); Stephane Rioux, Beauport (CA); Bernard R. Brodeur, Sillery (CA); Josee Hamel, Sillery (CA); Patrick Rheault, St-Etienne-de-Lauzon (CA)

(73) Assignee: ID Biomedical Corporation, Laval (CA)

( * ) Notice: Subject to any disclaimer, the term of this patent is extended or adjusted under 35 U.S.C. 154(b) by 0 days.

(21) Appl. No.: 10/078,531

(22) Filed: Feb. 21, 2002

(65) Prior Publication Data

US 2003/0049271 A1    Mar. 13, 2003

Related U.S. Application Data

(60) Provisional application No. 60/269,840, filed on Feb. 21, 2001.

(51) Int. Cl.
    *A61K 39/00*    (2006.01)
(52) U.S. Cl. .................................... 424/190.1; 530/350
(58) Field of Classification Search .............. 424/190.1, 424/185.1, 184.1, 234.1, 244.1; 530/330, 530/300, 350, 825; 514/2
    See application file for complete search history.

(56) References Cited

U.S. PATENT DOCUMENTS

2003/0170782 A1* 9/2003 Le Page et al. ............. 435/69.1

FOREIGN PATENT DOCUMENTS

| WO | WO 99/05293 | * | 10/1999 |
| WO | 01/32882 | * | 5/2001 |
| WO | WO 01/32882 | | 5/2001 |
| WO | 02/34771 A2 | | 5/2002 |
| WO | WO 02/088178 | | 11/2002 |
| WO | WO 02/092818 | | 11/2002 |
| WO | WO 03/093306 | | 11/2003 |
| WO | 2004/078907 A2 | | 9/2004 |

OTHER PUBLICATIONS

Rudikoff et al ,Proc Natl Acad Sci USA , vol. 79 pp. 1979-1983, Mar. 1982.*
Burgess et al. ,J of Cell Biology, vol. 111, pp. 2129-2138, Nov. 1990.*
Lazar et al ,Molecular and Cellular Biology, vol. 8, pp. 1247-1252, Mar. 1988.*
Sequence alignment SEQ ID No. 2.*
The Dictionary of Immunology, Herbert et al eds, Academic Press, 1995.*
Feng et al (Infection and Immunity, 64(1):363-365, 1996).*
Ellis, R.W. (Chapter 29 of "Vaccines" [Plotkin, S.A. et al. (eds) published by W. B. Saunders company (Philadelphia) in 1988, especially p. 571, 2nd full paragraph].*
Rudinger et al, in "Peptide Hormones", edited by Parsons, J.A., University Park Press, Jun. 1976, p. 6.*
Burgess et al., The Journal of Cell Biology, 111:2129-2138, 1990).*
Lazar et al., Molecular and Cellular Biology, 8(3):1247-1252, 1988.*
Jobling et al. (Mol. Microbiol., 1991, 5(7):1755-67).*
Ferretti et al (PNAS, 98(8):4658-4663, Apr. 10, 2001).*
Dixon et al, PIR__79 Database Accession No. T51594, Dixon et al, Aug. 18, 2000.*
McDonald on et al, PIR__79 Database Accession No. JE0176, Jul. 3, 1998.*
Harlow et al, Antibodies:A Laboratory Manual, Cold Spring Harbor Press, 1988; Chapter 5, pp. 72-73, 76-77.*
Campbell et al IN:Monoclaonal Antibody Technology, Elsevier Science Publishers, 1984, Chapter 1, section 1.3.4. p. 29.*
Analysis of Gene Expression in *Streptococcus pyogenes* by Quantitative Polymerase Chain Reaction; Leslie Croy, Stephen Olmsted, 2002 General Meeting (May 19, 2002-May 23, 2002) American Society for Microbiology.
Utilization of Human Antibodies to Open Reading Frame Proteins for Evaluating Opsonophagocytic Activity Against *Streptococcus pyogenes*; Eliszabeth Anderson et al., 2002 General Meeting (May 19, 2002-May 23, 2002) American Society for Microbiology.
Reid et al., "Postgenomic analysis of 4 novel antigens of group A streptococcus", Journal of Bacteriology, vol. 184, No. 22, pp. 6316-6324, Nov. 2002.
Virtaneva et al., "GAS Gene Expression in Humans and Cynomolgus Macaques with Acute Pharyngitis", Infection and Immunity, vol. 71, No. 4, pp. 2219-2207, Apr. 2003.
Database Swall—Jun. 1, 2001 Accession No. Q9A0C0—XP002210858 "Complete genome sequence of an M1 strain of streptococcus pyogenes." Ferretti, Joseph J. et al.
Drew, "A central control for ess"Bell Laboratories record, Bell telephone laboratories inc. Murray Hill, New Jersey, US—Feb. 1960 p. 49-53XP000838613—Abstract.
Journal of clinical investigation May 1999, vol. 103, No. 9, pp. 1261-1268 ISSN: 0021-9738, XP000906814 "New protective antigen of group A streptococci" Abstract, Dale, James B. et al.
Sharma A. et al "Cloning, Expression, and Sequencing of a Cell Surface Antigen Containing a Leucine-Rich Repeat Motif from *Bacteroides forsythus* ATCC 43037" Infection and Immunity, vol. 66, No. 12, Dec. 1998, p. 5703-5710.
Sánchez-Beato A.R. et al "Molecular characterization of PcpA: a novel choline-binding protein of *Streptococcus pneumoniae*" FEMS Microbiology Letters 164 (1998) 207-214.
Reid S.D. et al "Multilocus analysis of extracellular putative virulence proteins made by group A *Streptococcus*: Population genetics human serologic response, and gene transcription" PNAS, vol. 98, No. 13, Jun. 19, 2001 p. 7552-7557.

(Continued)

*Primary Examiner*—Patricia A Duffy
(74) *Attorney, Agent, or Firm*—Seed IP Law Group PLLC

(57) ABSTRACT

The present invention relates to antigens, more particularly antigens of *Streptococcus pyogenes* (also called group A *Streptococcus* (GAS)) bacterial pathogen which are useful as vaccine component for prophylaxis, therapy and/or diagnostic.

6 Claims, 6 Drawing Sheets

OTHER PUBLICATIONS

Ferretti J.J. et al "Complete genome sequence of an M1 strain of *Streptococcus pyogenes*" *PNAS*, vol. 98, No. 8, Apr. 10, 2001 p. 4658-4663.

Janulczyk R. and Rasmussen M. "Improved Pattern for Genome-Based Screening Identifies Novel Cell Wall-Attached Proteins in Gram-Posivite Bacteria" *Infection and Immunity*, Jun. 2001, p. 4019-4026, vol. 69, No. 6.

Reid S.D. et al "Group A *Streptococcus*: allelic variation, population genetics, and host-pathogen interactions" *The Journal of Clinical Investigation*, Feb. 2001, vol. 107, No. 4, p. 393-399.

Reid S.D. et al., ASM 101st General Meeting, Orlando, Florida, Session 130/D. Abstract D-155, May 22, 2001.

Smoot J. C., et al., "Genome sequence and comparative microarray analysis of serotype M18 group A Streptococcus strains associated with acute rheumatic fever outbreaks." Apr. 2, 2002, *PNAS* vol. 99, No. 7, p. 4668-4673 + supplementary material.

* cited by examiner

Figure 1

```
   1 ATGAAGAAAC ATCTTAAAAC AGTTGCCTTG ACCCTCACTA CAGTATCGGT AGTCACCCAC
  61 AATCAGGAAG TTTTTAGTTT AGTCAAAGAG CCAATTCTTA AACAAACTCA AGCTTCTTCA
 121 TCGATTTCTG GCGCTGACTA CGCAGAAAGT AGCGGTAAAA GCAAGTTAAA GATTAATGAA
 181 ACTTCTGGCC CTGTTGATGA TACAGTCACT GACTTATTTT CGGATAAACG TACTACTCCT
 241 GAAAAAATAA AAGATAATCT TGCTAAAGGT CCGAGAGAAC AAGAGTTAAA GGCAGTAACA
 301 GAGAATACAG AATCAGAAAA GCAGATCACT TCTGGATCTC AACTAGAACA ATCAAAAGAG
 361 TCTCTTTCTT TAAATAAAAC AGTGCCATCA ACGTCTAATT GGGAGATTTG TGATTTATT
 421 ACTAAGGGGA ATACCCTTGT TGGTCTTTCA AAATCAGGTG TTGAAAAGTT ATCTCAAACT
 481 GATCATCTCG TATTGCCTAG TCAAGCAGCA GATGGAACTC AATTGATACA AGTAGCTAGT
 541 TTTGCTTTTA CTCCAGATAA AAGACGGCA ATTGCAGAAT ATACCAGTAG GGCTGGAGAA
 601 AATGGGGAAA TAAGCCAACT AGATGTGGAT GGAAAAGAAA TTATTAACGA AGGTGAGGTT
 661 TTTAATTCTT ATCTACTAAA GAAGGTAACA ATCCCAACTG GTTATAAACA TATTGGTCAA
 721 GATGCTTTTG TGGACAATAA GAATATTGCT GAGGTTAATC TTCCTGAAAG CCTCGAGACT
 781 ATTTCTGACT ATGCTTTTGC TCACCTAGCT TTGAAACAGA TCGATTTGCC AGATAATTTA
 841 AAAGCGATTG GAGAATTAGC TTTTTTTGAT AATCAAATTA CAGGTAAACT TTCTTTGCCA
 901 CGTCAGTTAA TGCGATTAGC AGAACGTGCT TTTAAATCAA ACCATATCAA AACAATTGAG
 961 TTTAGAGCAA ATAGTCTAAA AGTGATAGGG GAAGCTAGTT TTCAAGATAA TGATCTGAGT
1021 CAACTAATGC TACCTGACGG TCTTGAAAAA ATAGAATCAG AAGCTTTTAC AGGAAATCCA
1081 GGAGATGATC ACTACAATAA CCGTGTTGTT TTGTGGACAA AATCTGGAAA AAATCCTTCT
1141 GGTCTTGCTA CTGAAAATAC CTATGTTAAT CCTGATAAGT CACTATGGCA GGAAAGTCCT
1201 GAGATTGATT ATACTAAATG GTTAGAGGAA GATTTTACCT ATCAAAAAAA TAGTGTTACA
1261 GGTTTTTCAA ATAAAGGCTT ACAAAAAGTA AAACGTAATA AAAACTTAGA AATTCCAAAA
1321 CAGCACAATG GTGTTACTAT TACTGAAATT GGTGATAATG CTTTTCGCAA TGTTGATTTT
1381 CAAAATAAAA CTTTACGTAA ATATGATTTG GAAGAAGTAA AGCTTCCCTC AACTATTCGG
1441 AAAATAGGTG CTTTTGCTTT TCAATCTAAT AACTTGAAAT CTTTTGAAGC AAGTGACGAT
1501 TTAGAAGAGA TTAAAGAGGG AGCCTTTATG AATAATCGTA TTGAAACCTT GGAATTAAAA
1561 GATAAATTAG TTACTATTGG TGATGCGGCT TTCCATATTA ATCATATTTA TGCCATTGTT
1621 CTTCCAGAAT CTGTACAACA AATAGGGCGT TCAGCATTTC GGCAAATGG TGCAAATAAT
1681 CTTATTTTTA TGGGAAGTAA GGTTAAGACC TTAGGTGAGA TGGCATTTTT ATCAAATAGA
1741 CTTGAACATC TGGATCTTTC TGAGCAAAAA CAGTTAACAG AGATTCCTGT TCAAGCCTTT
1801 TCAGACAATG CCTTGAAAGA AGTATTATTA CCAGCATCAC TGAAAACGAT TCGAGAAGAA
1861 GCCTTCAAAA AGAATCATTT AAAACAACTG GAAGTGGCAT CTGCCTTGTC CCATATTGCT
1921 TTTAATGCTT TAGATGATAA TGATGGTGAT GAACAATTTG ATAATAAAGT GGTTGTTAAA
1981 ACGCATCATA ATTCCTACGC ACTAGCAGAT GGTGAGCATT TTATCGTTGA TCCAGATAAG
2041 TTATCTTCTA CAATAGTAGA CCTTGAAAAG ATTTTAAAAC TAATCGAAGG TTTAGATTAT
2101 TCTACATTAC GTCAGACTAC TCAAACTCAG TTTAGAGACA TGACTACTGC AGGTAAAGCG
2161 TTGTTGTCAA AATCTAACCT CCGACAAGGA GAAAAACAAA AATTCCTTCA AGAAGCACAA
2221 TTTTTCCTTG GCCGCGTTGA TTTGGATAAA GCCATAGCTA AAGCTGAGAA GGCTTTAGTG
2281 ACCAAGAAGG CAACAAAGAA TGGTCAGTTG CTTGAAAGAA GTATTAACAA AGCGGTATTA
2341 GCTTATAATA ATAGCGCTAT TAAAAAAGCT AATGTTAAGC GCTTGGAAAA AGAGTTAGAC
2401 TTGCTAACAG GATTAGTTGA GGGAAAAGGA CCATTAGCGC AAGCTACAAT GGTACAAGGA
2461 GTTTATTTAT TAAAGACGCC TTTGCCATTG CCAGAATATT ATATCGGATT GAACGTTTAT
2521 TTTGACAAGT CTGGAAAATT GATTTATGCA CTTGATATGA GTGATACTAT TGGCGAGGGA
2581 CAAAAAGACG CTTATGGTAA TCCTATATTA AATGTTGACG AGGATAATGA AGGTTATCAT
2641 GCCTTGGCAG TTGCCACTTT AGCTGATTAT GAGGGGCTCG ACATCAAAAC AATTTTAAAT
2701 AGTAAGCTTA GTCAATTAAC ATCTATTCGT CAGGTACCGA CTGCAGCCTA TCATAGAGCC
2761 GGTATTTTCC AAGCTATCCA AAATGCAGCG GCAGAAGCAG AGCAGTTATT GCCTAAACCA
2821 GGTACGCACT CTGAGAAGTC AAGCTCAAGT GAATCTGCTA ACTCTAAAGA TAGAGGATTG
2881 CAATCAAACC CAAAAACGAA TAGAGGACGA CACTCTGCAA TATTGCCTAG GACAGGGTCA
2941 AAAGGCAGCT TTGTCTATGG AATCTTAGGT TACACTAGCG TTGCTTTACT GTCACTAATA
3001 ACTGCTATAA AAAGAAAAA ATATTAA
```

Figure 2

```
  1 MKKHLKTVAL TLTTVSVVTH NQEVFSLVKE PILKQTQASS SISGADYAES SGKSKLKINE
 61 TSGPVDDTVT DLFSDKRTTP EKIKDNLAKG PREQELKAVT ENTESEKQIT SGSQLEQSKE
121 SLSLNKTVPS TSNWEICDFI TKGNTLVGLS KSGVEKLSQT DHLVLPSQAA DGTQLIQVAS
181 FAFTPDKKTA IAEYTSRAGE NGEISQLDVD GKEIINEGEV FNSYLLKKVT IPTGYKHIGQ
241 DAFVDNKNIA EVNLPESLET ISDYAFAHLA LKQIDLPDNL KAIGELAFFD NQITGKLSLP
301 RQLMRLAERA FKSNHIKTIE FRGNSLKVIG EASFQDNDLS QLMLPDGLEK IESEAFTGNP
361 GDDHYNNRVV LWTKSGKNPS GLATENTYVN PDKSLWQESP EIDYTKWLEE DFTYQKNSVT
421 GFSNKGLQKV KRNKNLEIPK QHNGVTITEI GDNAFRNVDF QNKTLRKYDL EEVKLPSTIR
481 KIGAFAFQSN NLKSFEASDD LEEIKEGAFM NNRIETLELK DKLVTIGDAA FHINHIYAIV
541 LPESVQEIGR SAFRQNGANN LIFMGSKVKT LGEMAFLSNR LEHLDLSEQK QLTEIPVQAF
601 SDNALKEVLL PASLKTIREE AFKKNHLKQL EVASALSHIA FNALDDNDGD EQFDNKVVVK
661 THHNSYALAD GEHFIVDPDK LSSTIVDLEK ILKLIEGLDY STLRQTTQTQ FRDMTTAGKA
721 LLSKSNLRQG EKQKFLQEAQ FFLGRVDLDK AIAKAEKALV TKKATKNGQL LERSINKAVL
781 AYNNSAIKKA NVKRLEKELD LLTGLVEGKG PLAQATMVQG VYLLKTPLPL PEYYIGLNVY
841 FDKSGKLIYA LDMSDTIGEG QKDAYGNPIL NVDEDNEGYH ALAVATLADY EGLDIKTILN
901 SKLSQLTSIR QVPTAAYHRA GIFQAIQNAA AEAEQLLPKP GTHSEKSSSS ESANSKDRGL
961 QSNPKTNRGR HSAILPRTGS KGSFVYGILG YTSVALLSLI TAIKKKKY*
```

Figure 3A

Clustal W(1.4) multiple sequence alignment

7 Sequences Aligned.          Alignment Score = 118839
Gaps Inserted = 0             Conserved Identities = 936

Pairwise Alignment Mode: Fast
Pairwise Alignment Parameters:
    ktup = 1   Gap Penalty = 3   Top Diagonals = 5   Window Size = 5

Multiple Alignment Parameters:
    Open Gap Penalty = 10.0   Extend Gap Penalty = 0.1
    Delay Divergent = 40%     Gap Distance = 8
    Similarity Matrix: blosum Processing time: 12.9 seconds

```
Spy74_M3     1                                               DYAES    5
Spy70_M5     1                          LVKEPILKQTQASSSISGADYAES   24
Spy69_M6     1                                 KQTQASSSISGADYAES   17
Spy68_M2     1                          LVKEPILKQTQASSSISGADYAES   24
Spy60_M1     1                          LVKEPILKQTQASSSISGADYAES   24
12357_M18    1                           VKEPILKQTQASSSISGADYAES   23
700294_M1    1 MKKHLKTVALTLTTVSVVTHNQEVFSLVKEPILKQTQASSSISGADYAES   50
                                                            *****

Spy74_M3     6 SGKSKLKINETSGPVDDTVTDLFSDKRTTPEKIKDNLAKGPREQELKAVT   55
Spy70_M5    25 SGKSKLKINETSGPVDDTVTDLFSDKRTTPEKIKDNLAKGPREQELKAVT   74
Spy69_M6    18 SGKSKLKINETSGPVDDTVTDLFSDKRTTPEKIKDNLAKGPREQELKAVT   67
Spy68_M2    25 SGKSKLKINETSGPVDDTVTDLFSDKRTTPEKIKDNLAKGPREQELKTVT   74
Spy60_M1    25 SGKSKLKINETSGPVDDTVTDLFSDKRTTPEKIKDNLAKGPREQELKAVT   74
12357_M18   24 SGKSKLKINETSGPVDDTVTDLFSDKRTTPEKIKDNLAKGPREQELKAVT   73
700294_M1   51 SGKSKLKINETSGPVDDTVTDLFSDKRTTPEKIKDNLAKGPREQELKAVT  100
               ************************************************ **

Spy74_M3    56 ENTESEKQITSGSQLEQSKESLSLNKRVPSTSNWEICDFITKGNTLVGLS  105
Spy70_M5    75 ENTESEKQINSGSQLEQSKESLSLNKRVPSTSNWEICDFITKGNTLVGLS  124
Spy69_M6    68 ENTESEKQINSGSQLEQSKESLSLNKRVPSTSNWEICDFITKGNTLVGLS  117
Spy68_M2    75 ENTESEKQITSGSQLEQSKESLSLNKTVPSTSNWEICDFITKGNTLVGLS  124
Spy60_M1    75 ENTESEKQITSGSQLEQSKESLSLNKTVPSTSNWEICDFITKGNTLVGLS  124
12357_M18   74 ENTESEKQINSGSQLEQSKESLSLNKRVPSTSNWEICDFITKGNTLVGLS  123
700294_M1  101 ENTESEKQITSGSQLEQSKESLSLNKTVPSTSNWEICDFITKGNTLVGLS  150
               ******** ****************** *********************

Spy74_M3   106 KSGVEKLSQTDHLVLPSQAADGTQLIQVASFAFTPDKKTAIAEYTSRAGE  155
Spy70_M5   125 KSGVEKLSQTDHLVLPSQAADGTQLIQVASFAFTPDKKTAIAEYTSRAGE  174
Spy69_M6   118 KSGVEKLSQTDHLVLPSQAADGTQLIQVASFAFTPDKKTAIAEYTSRAGE  167
Spy68_M2   125 KSGVEKLSQTDHLVLPSQAADGTQLIQVASFAFTPDKKTAIAEYTSRAGE  174
Spy60_M1   125 KSGVEKLSQTDHLVLPSQAADGTQLIQVASFAFTPDKKTAIAEYTSRAGE  174
12357_M18  124 KSGVEKLSQTDHLVLPSQAADGTQLIQVASFAFTPDKKTAIAEYTSRAGE  173
700294_M1  151 KSGVEKLSQTDHLVLPSQAADGTQLIQVASFAFTPDKKTAIAEYTSRAGE  200
               *************************************************
```

Figure 3B

| | | | |
|---|---|---|---|
| Spy74_M3 | 156 | NGEISQLDVDGKEIINEGEVFNSYLLKKVTIPTGYKHIGQDAFVDNKNIA | 205 |
| Spy70_M5 | 175 | NGEISQLDVDGKEIINEGEVFNSYLLKKVTIPTGYKHIGQDAFVDNKNIA | 224 |
| Spy69_M6 | 168 | NGEISQLDVDGKEIINEGEVFNSYLLKKVTIPTGYKHIGQDAFVDNKNIA | 217 |
| Spy68_M2 | 175 | NGEISQLDVDGKEIINEGEVFNSYLLKKVTIPTGYKHIGQDAFVDNKNIA | 224 |
| Spy60_M1 | 175 | NGEISQLDVDGKEIINEGEVFNSYLLKKVTIPTGYKHIGQDAFVDNKNIA | 224 |
| 12357_M18 | 174 | NGEISQLDVDGKEIINEGEVFNSYLLKKVTIPTGYKHIGQDAFVDNKNIA | 223 |
| 700294_M1 | 201 | NGEISQLDVDGKEIINEGEVFNSYLLKKVTIPTGYKHIGQDAFVDNKNIA | 250 |
| | | ************************************************** | |

| | | | |
|---|---|---|---|
| Spy74_M3 | 206 | EVNLPESLETISDYAFAHLALKQIDLPDNLKAIGELAFFDNQITGKLSLP | 255 |
| Spy70_M5 | 225 | EVNLPESLETISDYAFAHLALKQIDLPDNLKAIGELAFFDNQITGKLSLP | 274 |
| Spy69_M6 | 218 | EVNLPESLETISDYAFAHLALKQIDLPDNLKAIGELAFFDNQITGKLSLP | 267 |
| Spy68_M2 | 225 | EVNLPESLETISDYAFAHLALKQIDLPDNLKAIGELAFFDNQITGKLSLP | 274 |
| Spy60_M1 | 225 | EVNLPESLETISDYAFAHLALKQIDLPDNLKAIGELAFFDNQITGKLSLP | 274 |
| 12357_M18 | 224 | EVNLPESLETISDYAFAHLALKQIDLPDNLKAIGELAFFDNQITGKLSLP | 273 |
| 700294_M1 | 251 | EVNLPESLETISDYAFAHLALKQIDLPDNLKAIGELAFFDNQITGKLSLP | 300 |
| | | ************************************************** | |

| | | | |
|---|---|---|---|
| Spy74_M3 | 256 | RQLMRLAERAFKSNHIKTIEFRGNSLKVIGEASFQDNDLSQLMLPDGLEK | 305 |
| Spy70_M5 | 275 | RQLMRLAERAFKSNHIKTIEFRGNSLKVIGEASFQDNDLSQLMLPDGLEK | 324 |
| Spy69_M6 | 268 | RQLMRLAERAFKSNHIKTIEFRGNSLKVIGEASFQDNDLSQLMLPDGLEK | 317 |
| Spy68_M2 | 275 | RQLMRLAERAFKSNHIKTIEFRGNSLKVIGEASFQDNDLSQLMLPDGLEK | 324 |
| Spy60_M1 | 275 | RQLMRLAERAFKSNHIKTIEFRGNSLKVIGEASFQDNDLSQLMLPDGLEK | 324 |
| 12357_M18 | 274 | RQLMRLAERAFKSNHIKTIEFRGNSLKVIGEASFQDNDLSQLMLPDGLEK | 323 |
| 700294_M1 | 301 | RQLMRLAERAFKSNHIKTIEFRGNSLKVIGEASFQDNDLSQLMLPDGLEK | 350 |
| | | ************************************************** | |

| | | | |
|---|---|---|---|
| Spy74_M3 | 306 | IESEAFTGNPGDDHYNNRVVLWTKSGKNPYGLATENTYVNPDKSLWQESP | 355 |
| Spy70_M5 | 325 | IESEAFTGNPGDDHYNNRVVLWTKSGKNPYGLATENTYVNPDKSLWQESP | 374 |
| Spy69_M6 | 318 | IESEAFTGNPGDDHYNNRVVLWTKSGKNPYGLATENTYVNPDKSLWQESP | 367 |
| Spy68_M2 | 325 | IESEAFTGNPGDDHYNNRVVLWTKSGKNPSGLATENTYVNPDKSLWQESP | 374 |
| Spy60_M1 | 325 | IESEAFTGNPGDDHYNNRVVLWTKSGKNPSGLATENTYVNPDKSLWQESP | 374 |
| 12357_M18 | 324 | IESEAFTGNPGDDHYNNRVVLWTKSGKNPYGLATENTYVNPDKSLWQESP | 373 |
| 700294_M1 | 351 | IESEAFTGNPGDDHYNNRVVLWTKSGKNPSGLATENTYVNPDKSLWQESP | 400 |
| | | ****************************** ******************* | |

| | | | |
|---|---|---|---|
| Spy74_M3 | 356 | EIDYTKWLEEDFTYQKNSVTGFSSKGLQKVKRNKNLEIPKQHNGVTITEI | 405 |
| Spy70_M5 | 375 | EIDYTKWLEEDFTYQKNSVTGFSSKGLQKVKRNKNLEIPKQHNGVTITEI | 424 |
| Spy69_M6 | 368 | EIDYTKWLEEDFTYQKNSVTGFSSKGLQKVKRNKNLEIPKQHNGVTITEI | 417 |
| Spy68_M2 | 375 | EIDYTKWLEEDFTYQKNSVTGFSNKGLQKVKRNKNLEIPKQHNGVTITEI | 424 |
| Spy60_M1 | 375 | EIDYTKWLEEDFTYQKNSVTGFSNKGLQKVKRNKNLEIPKQHNGVTITEI | 424 |
| 12357_M18 | 374 | EIDYTKWLEEDFTYQKNSVTGFSSKGLQKVKRNKNLEIPKQHNGVTITEI | 423 |
| 700294_M1 | 401 | EIDYTKWLEEDFTYQKNSVTGFSNKGLQKVKRNKNLEIPKQHNGVTITEI | 450 |
| | | *********************** ************************** | |

| | | | |
|---|---|---|---|
| Spy74_M3 | 406 | GDNAFRNVDFQNKTLRKYDLEEVKLPSTIRKIGAFAFQSNNLKSFEASDD | 455 |
| Spy70_M5 | 425 | GDNAFRNVDFQNKTLRKYDLEEVKLPSTIRKIGAFAFQSNNLKSFEASDD | 474 |
| Spy69_M6 | 418 | GDNAFRNVNFQNKTLRKYDLEEVKLPSTIRKIGAFAFQSNNLKSFEASDD | 467 |
| Spy68_M2 | 425 | GDNAFRNVDFQNKTLRKYDLEEVKLPSTIRKIGAFAFQSNNLKSFEASDD | 474 |
| Spy60_M1 | 425 | GDNAFRNVDFQNKTLRKYDLEEVKLPSTIRKIGAFAFQSNNLKSFEASDD | 474 |
| 12357_M18 | 424 | GDNAFRNVDFQNKTLRKYDLEEVKLPSTIRKIGAFAFQSNNLKSFEASDD | 473 |
| 700294_M1 | 451 | GDNAFRNVDFQNKTLRKYDLEEVKLPSTIRKIGAFAFQSNNLKSFEASDD | 500 |
| | | ******** ***************************************** | |

Figure 3C

```
Spy74_M3    456 LEEIKEGAFMNNRIETLELKDKLVTIGDAAFHINHIYAIVLPESVQEIGR 505
Spy70_M5    475 LEEIKEGAFMNNRIETLELKDKLVTIGDAAFHINHIYAIVLPESVQEIGR 524
Spy69_M6    468 LEEIKEGAFMNNRIETLELKDKLVTIGDAAFHINHIYAIVLPESVQEIGR 517
Spy68_M2    475 LEEIKEGAFMNNRIETLELKDKLVTIGDAAFHINHIYAIVLPESVQEIGR 524
Spy60_M1    475 LEEIKEGAFMNNRIETLELKDKLVTIGDAAFHINHIYAIVLPESVQEIGR 524
12357_M18   474 LEEIKEGAFMNNRIETLELKDKLVTIGDAAFHINHIYAIVLPESVQEIGR 523
700294_M1   501 LEEIKEGAFMNNRIETLELKDKLVTIGDAAFHINHIYAIVLPESVQEIGR 550
                **************************************************

Spy74_M3    506 SAFRQNGANNLIFMGSKVKTIGEMAFLSNRLEHLDLSEQKQLTEIPVQAF 555
Spy70_M5    525 SAFRQNGANNLIFMGSKVKTLGEMAFLSNRLEHLDLSEQKQLTEIPVQAF 574
Spy69_M6    518 SAFRQNGANNLIFMGSKVKTLGEMAFLSNRLEHLDLSEQKQLTEIPVQAF 567
Spy68_M2    525 SAFRQNGANNLIFMGSKVKTLGEMAFLSNRLEHLDLSEQKQLTEIPVQAF 574
Spy60_M1    525 SAFRQNGANNLIFMGSKVKTLGEMAFLSNRLEHLDLSEQKQLTEIPVQAF 574
12357_M18   524 SAFRQNGANNLIFMGSKVKTLGEMAFLSNRLEHLDLSEQKQLTEIPVQAF 573
700294_M1   551 SAFRQNGANNLIFMGSKVKTLGEMAFLSNRLEHLDLSEQKQLTEIPVQAF 600
                ******************** *****************************

Spy74_M3    556 SDNALKEVLLPASLKTIREEAFKKNHLKQLEVASALSHIAFNALDDNDGD 605
Spy70_M5    575 SDNALKEVLLPASLKTIREEAFKKNHLKQLEVASALSHIAFNALDDNDGD 624
Spy69_M6    568 SDNALKEVLLPASLKTIREEAFKKNHLKQLEVASALSHIAFNALDDNDGD 617
Spy68_M2    575 SDNALKEVLLPASLKTIREEAFKKNHLKQLEVASALSHIAFNALDDNDGD 624
Spy60_M1    575 SDNALKEVLLPASLKTIREEAFKKNHLKQLEVASALSHIAFNALDDNDGD 624
12357_M18   574 SDNALKEVLLPASLKTIREEAFKKNHLKQLEVASALSHIAFNALDDNDGD 623
700294_M1   601 SDNALKEVLLPASLKTIREEAFKKNHLKQLEVASALSHIAFNALDDNDGD 650
                **************************************************

Spy74_M3    606 EQFDNKVVVKTHHNSYALADGEHFIVDPDKLSSTMVDLEKILKLIEGLDY 655
Spy70_M5    625 EQFDNKVVVKTHHNSYALADGEHFIVDPDKLSSTIVDLEKILKLIEGLDY 674
Spy69_M6    618 EQFDNKVVVKTHHNSYALADGEHFIVDPDKLSSTIVDLEKILKLIEGLDY 667
Spy68_M2    625 EQFDNKVVVKTHHNSYALADGEHFIVDPDKLSSTMIDLEKILKLIEGLDY 674
Spy60_M1    625 EQFDNKVVVKTHHNSYALADGEHFIVDPDKLSSTIVDLEKILKLIEGLDY 674
12357_M18   624 EQFDNKVVVKTHHNSYALADGEHFIVDPDKLSSTIVDLEKILKLIEGLDY 673
700294_M1   651 EQFDNKVVVKTHHNSYALADGEHFIVDPDKLSSTIVDLEKILKLIEGLDY 700
                **********************************  **************

Spy74_M3    656 STLRQTTQTQFRDMTTAGKALLSKSKLRQGEKQKFLQEAQFFLGRVDLDK 705
Spy70_M5    675 STLRQTTQTQFRDMTTAGKALLSKSNLRQGEKQKFLQEAQFFLGRVDLDK 724
Spy69_M6    668 STLRQTTQTQFRDMTTAGKALLSKSNLRQGEKQKFLQEAQFFLGRVDLDK 717
Spy68_M2    675 STLRQTTQTQFRDMTTAGKALLSKSNLRQGEKQKFLQEAQFFLGRVDLDK 724
Spy60_M1    675 STLRQTTQTQFRDMTTAGKALLSKSNLRQGEKQKFLQEAQFFLGRVDLDK 724
12357_M18   674 STLRQTTQTQFRDMTTAGKALLSKSNLRQGEKQKFLQEAQFFLGRVDLDK 723
700294_M1   701 STLRQTTQTQFRDMTTAGKALLSKSNLRQGEKQKFLQEAQFFLGRVDLDK 750
                ************************ *************************

Spy74_M3    706 AIAKAEKALVTKKATKNGQLLGRSINKAVLAYNNSAIKKANVKRLEKELD 755
Spy70_M5    725 AIAKAEKALVTKKATKNGQLLERSINKAVLAYNNSAIKKANVKRLEKELD 774
Spy69_M6    718 AIAKAEKALVTKKATKNGQLLERSINKAVSAYNNSAIKKANVKRLEKELD 767
Spy68_M2    725 AIAKAEKALVTKKATKNGQLLERSINKAVLAYNNSAIKKANVKRLEKELD 774
Spy60_M1    725 AIAKAEKALVTKKATKNGQLLERSINKAVLAYNNSAIKKANVKRLEKELD 774
12357_M18   724 AIAKAEKALVTKKATKNGQLLERSINKAVLAYNNSAIKKANVKRLEKELD 773
700294_M1   751 AIAKAEKALVTKKATKNGQLLERSINKAVLAYNNSAIKKANVKRLEKELD 800
                ******************** ******* *********************
```

Figure 3D

| | | | |
|---|---|---|---|
| Spy74_M3 | 756 | LLTGLVEGKGPLAQATMVQGVYLLKTPLPLPEYYIGLNVYFDKSGKLIYA | 805 |
| Spy70_M5 | 775 | LLTGLVEGKGPLAQATMVQGVYLLKTPLPLPEYYIGLNVYFDKSGKLIYA | 824 |
| Spy69_M6 | 768 | LLTGLVEGKGPLAQATMVQGVYLLKTPLPLPEYYIGLNVYFDKSGKLIYA | 817 |
| Spy68_M2 | 775 | LLTGLVEGKGPLAQATMVQGVYLLKTPLPLPEYYIGLNVYFDKSGKLIYA | 824 |
| Spy60_M1 | 775 | LLTGLVEGKGPLAQATMVQGVYLLKTPLPLPEYYIGLNVYFDKSGKLIYA | 824 |
| 12357_M18 | 774 | LLTGLVEGKGPLAQATMVQGVYLLKTPLPLPEYYIGLNVYFDKSGKLIYA | 823 |
| 700294_M1 | 801 | LLTGLVEGKGPLAQATMVQGVYLLKTPLPLPEYYIGLNVYFDKSGKLIYA | 850 |
| | | ************************************************** | |

| | | | |
|---|---|---|---|
| Spy74_M3 | 806 | LDMSDTIGEGQKDAYGNPILNVDEDNEGYHALAVATLADYEGLDIKTILN | 855 |
| Spy70_M5 | 825 | LDMSDTIGEGQKDAYGNPILNVDEDNEGYHALAVATLADYEGLDIKTILN | 874 |
| Spy69_M6 | 818 | LDMSDTIGEGQKDAYGNPILNVDEDNEGYHALAVATLADYEGLDIKTILN | 867 |
| Spy68_M2 | 825 | LDMSDTIGEGQKDAYGNPILNVDEDNEGYHALAVATLADYEGLDIKTILN | 874 |
| Spy60_M1 | 825 | LDMSDTIGEGQKDAYGNPILNVDEDNEGYHALAVATLADYEGLDIKTILN | 874 |
| 12357_M18 | 824 | LDMSDTIGEGQKDAYGNPILNVDEDNEGYHALAVATLADYEGLDIKTILN | 873 |
| 700294_M1 | 851 | LDMSDTIGEGQKDAYGNPILNVDEDNEGYHALAVATLADYEGLDIKTILN | 900 |
| | | ************************************************** | |

| | | | |
|---|---|---|---|
| Spy74_M3 | 856 | SKLSQLTSIRQVPTAAYHRAGIFQAIQNAAAEAEQLLPKPGTHSEKSSSS | 905 |
| Spy70_M5 | 875 | SKLSQLTSIRQVPTAAYHRAGIFQAIQNAAAEAEQLLPKAGTHSEKSSSS | 924 |
| Spy69_M6 | 868 | SKLSQLTSIRQVPTAAYHRAGIFQAIQNAAAEAEQLLPKPGTHSEKSSSS | 917 |
| Spy68_M2 | 875 | SKLSQLTSIRQVPTAAYHRAGIFQAIQNAAAEAEQLLPKPGMHSEKSSSS | 924 |
| Spy60_M1 | 875 | SKLSQLTSIRQVPTAAYHRAGIFQAIQNAAAEAEQLLPKPGTHSEKSSSS | 924 |
| 12357_M18 | 874 | SKLSQLTSIRQVPTAAYHRAGIFQAIQNAAAEAEQLLPKPGTHSEKSSSS | 923 |
| 700294_M1 | 901 | SKLSQLTSIRQVPTAAYHRAGIFQAIQNAAAEAEQLLPKPGTHSEKSSSS | 950 |
| | | *************************************** * ******* | |

| | | | |
|---|---|---|---|
| Spy74_M3 | 906 | ESANSKDRGLQSNPKTNRGRHSAILPRTGSKGSFVYGILGYTSVAL | 951 |
| Spy70_M5 | 925 | ESANSKDRGLQSNPKTNRGRHSAILPRTGSKGSFVYGILGYTSVAL | 970 |
| Spy69_M6 | 918 | ESANSKDRGLQSNPKTNRGRHSAILPRTGSKGSFVYGILGYTSVAL | 963 |
| Spy68_M2 | 925 | ESANSKDRGLQSHPKTNRGRHSAILPRTGSKGSFVYGILGYTSVALL | 971 |
| Spy60_M1 | 925 | ESANSKDRGLQSNPKTNRGRHSAILPRTGSKGSFVYGILGYTSVALL | 971 |
| 12357_M18 | 924 | ESANSKDRGLQSNPKTNRGRHSAILPRTGSKGSFVYGILGYTSVAL | 969 |
| 700294_M1 | 951 | ESANSKDRGLQSNPKTNRGRHSAILPRTGSKGSFVYGILGYTSVALLSLI | 1000 |
| | | *********** ********************************* | |

| | | | |
|---|---|---|---|
| Spy74_M3 | 952 | | 951 |
| Spy70_M5 | 971 | | 970 |
| Spy69_M6 | 964 | | 963 |
| Spy68_M2 | 972 | | 971 |
| Spy60_M1 | 972 | | 971 |
| 12357_M18 | 970 | | 969 |
| 700294_M1 | 1001 | TAIKKKKY | 1008 |

STREPTOCOCCUS PYOGENES POLYPEPTIDES AND CORRESPONDING DNA FRAGMENTS

This application claims the benefit of U.S. Provisional Application 60/269,840 filed Feb. 21, 2001, the disclosure of which is hereby incorporated by reference in its entirety.

FIELD OF THE INVENTION

The present invention is related to polypeptides of *Streptococcus pyogenes* (Group A *Streptococcus*) which may be used to prevent, diagnose and/or treat streptococcal infection.

BACKGROUND OF THE INVENTION

Streptococci are gram (+) bacteria which are differentiated by group specific carbohydrate antigens A through O which are found at the cell surface. *S. pyogenes* isolates are further distinguished by type-specific M protein antigens. M proteins are important virulence factors which are highly variable both in molecular weights and in sequences. Indeed, more than 80-M protein types have been identified on the basis of antigenic differences.

*S. pyogenes* is responsible for many diverse infection types, including pharyngitis, erysipelas and impetigo, scarlet fever, and invasive diseases such as bacteremia and necrotizing fasciitis. A resurgence of invasive disease in recent years has been documented in many countries, including those in North America and Europe. Although the organism is sensitive to antibiotics, the high attack rate and rapid onset of sepsis results in high morbidity and mortality.

To develop a vaccine that will protect hosts from *S. pyogenes* infection, efforts have focused on virulence factors such as the type-specific M proteins. However, the amino-terminal portion of M proteins was found to induce cross-reactive antibodies which reacted with human myocardium, tropomyosin, myosin, and vimentin, which might be implicated in autoimmune diseases. Others have used recombinant techniques to produce complex hybrid proteins containing amino-terminal peptides of M proteins from different serotypes. However, a safe vaccine containing all *S. pyogenes* serotypes will be highly complex to produce and standardize.

In addition to the serotype-specific antigens, other *S. pyogenes* proteins have generated interest as potential vaccine candidates. The C5a peptidase, which is expressed by at least *S. pyogenes* 40 serotypes, was shown to be immunogenic in mice, but its capacity to reduce the level of nasopharyngeal colonization was limited. Other investigators have also focused on the streptococcal pyrogenic exotoxins which appear to play an important role in pathogenesis of infection. Immunization with these proteins prevented the deadly symptoms of toxic shock, but did not prevent colonization.

The University of Oklahoma has set up a genome sequencing project for *S. pyogenes* strain M1 GAS.

Therefore there remains an unmet need for *S. pyogenes* antigens that may be used vaccine components for the prophylaxis and/or therapy of *S. pyogenes* infection.

SUMMARY OF THE INVENTION

According to one aspect, the present invention provides an isolated polynucleotide encoding a polypeptide having at least 70% identity to a second polypeptide comprising SEQ ID No: 2 or fragments or analogs thereof.

According to one aspect, the present invention relates to polypeptides which comprise an amino acid sequence SEQ ID No: 2 or fragments or analogs thereof.

In other aspects, there are provided polypeptides encoded by polynucleotides of the invention, pharmaceutical compositions, vectors comprising polynucleotides of the invention operably linked to an expression control region, as well as host cells transfected with said vectors and processes for producing polypeptides comprising culturing said host cells under conditions suitable for expression.

BRIEF DESCRIPTION OF THE DRAWINGS

FIG. 1 represents the DNA sequence (SEQ ID NO: 1) of BVH-P7 gene from serotype M1 *S. pyogenes* strain ATCC700294; SEQ ID NO: 1. The underlined portion of the sequence represents the region coding for the leader peptide.

FIG. 2 represents the amino acid sequence (SEQ ID NO: 2) BVH-P7 protein from serotype M1 *S. pyogenes* strain ATCC700294; SEQ ID NO: 2. The underline sequence represents the 21 amino acid residues leader peptide.

FIG. 3 depicts the comparison of the predicted amino acid sequences of the BVH-P7 open reading frames from Spy74, Spy70, Spy69, Spy68, Spy60, ATCC12357, ATCC700294 *S. pyogenes* strains by using the program Clustal W from MACVECTOR®-sequence analysis software (version 6.5). Underneath the alignment, there is a consensus line where * and . characters indicate identical and similar amino acid residues, respectively.

DETAILED DESCRIPTION OF THE INVENTION

The present invention provides purified and isolated polynucleotides, which encode Streptococcal polypeptides that may be used to diagnose, prevent, and/or treat Streptococcal infection.

According to one aspect, the present invention provides an isolated polynucleotide encoding a polypeptide having at least 70% identity to a second polypeptide comprising SEQ ID NO: 2 or fragments or analogs or thereof.

According to one aspect, the present invention provides an isolated polynucleotide encoding a polypeptide having at least 80% identity to a second polypeptide comprising SEQ ID NO: 2 or fragments or analogs or thereof.

According to one aspect, the present invention provides an isolated polynucleotide encoding a polypeptide having at least 90% identity to a second polypeptide comprising SEQ ID NO: 2 or fragments or analogs or thereof.

According to one aspect, the present invention provides an isolated polynucleotide encoding a polypeptide having at least 95% identity to a second polypeptide comprising SEQ ID NO: 2 or fragments or analogs or thereof.

According to one aspect, the present invention relates to polypeptides characterized by the amino acid sequence comprising SEQ ID NO: 2 or fragments or analogs or thereof.

According to one aspect, the present invention provides a polynucleotide encoding an epitope bearing portion of a polypeptide comprising SEQ ID NO: 2 or fragments or analogs or thereof.

According to one aspect, the present invention relates to epitope bearing portions of a polypeptide comprising SEQ ID NO: 2 or fragments or analogs or thereof.

According to one aspect, the present invention provides an isolated polynucleotide encoding a polypeptide having at least 70% identity to a second polypeptide comprising SEQ ID NO: 2.

According to one aspect, the present invention provides an isolated polynucleotide encoding a polypeptide having at least 80% identity to a second polypeptide comprising SEQ ID NO: 2.

According to one aspect, the present invention provides an isolated polynucleotide encoding a polypeptide having at least 90% identity to a second polypeptide comprising SEQ ID NO: 2.

According to one aspect, the present invention provides an isolated polynucleotide encoding a polypeptide having at least 95% identity to a second polypeptide comprising SEQ ID NO: 2.

According to one aspect, the present invention relates to polypeptides characterized by the amino acid sequence comprising SEQ ID NO: 2.

According to one aspect, the present invention provides a polynucleotide encoding an epitope bearing portion of a polypeptide comprising SEQ ID NO: 2.

According to one aspect, the present invention relates to epitope bearing portions of a polypeptide comprising SEQ ID NO: 2.

According to one aspect, the present invention provides an isolated polynucleotide comprising a polynucleotide chosen from:
(a) a polynucleotide encoding a polypeptide having at least 70% identity to a second polypeptide comprising a sequence chosen from: SEQ ID NO: 2 or fragments or analogs thereof;
(b) a polynucleotide encoding a polypeptide having at least 95% identity to a second polypeptide comprising a sequence chosen from: SEQ ID NO: 2 or fragments or analogs thereof;
(c) a polynucleotide encoding a polypeptide comprising a sequence chosen from: SEQ ID NO: 2 or fragments or analogs thereof;
(d) a polynucleotide encoding a polypeptide capable of generating antibodies having binding specificity for a polypeptide comprising a sequence chosen from: SEQ ID NO: 2 or fragments or analogs thereof;
(e) a polynucleotide encoding an epitope bearing portion of a polypeptide comprising a sequence chosen from SEQ ID NO: 2 or fragments or analogs thereof;
(f) a polynucleotide comprising a sequence chosen from SEQ ID NO: 1 or fragments or analogs thereof;
(g) a polynucleotide that is complementary to a polynucleotide in (a), (b), (c), (d), (e) or (f).

According to one aspect, the present invention provides an isolated polynucleotide comprising a polynucleotide chosen from:
(a) a polynucleotide encoding a polypeptide having at least 70% identity to a second polypeptide comprising a sequence chosen from: SEQ ID NO: 2;
(b) a polynucleotide encoding a polypeptide having at least 95% identity to a second polypeptide comprising a sequence chosen from: SEQ ID NO: 2;
(c) a polynucleotide encoding a polypeptide comprising a sequence chosen from: SEQ ID NO: 2;
(d) a polynucleotide encoding a polypeptide capable of raising antibodies having binding specificity for a polypeptide comprising a sequence chosen from: SEQ ID NO: 2;
(e) a polynucleotide encoding an epitope bearing portion of a polypeptide comprising a sequence chosen from SEQ ID NO: 2;
(f) a polynucleotide comprising a sequence chosen from SEQ ID NO: 1;
(g) a polynucleotide that is complementary to a polynucleotide in (a), (b), (c), (d), (e) or (f).

According to one aspect, the present invention provides an isolated polypeptide comprising a polypeptide chosen from:
(a) a polypeptide having at least 70% identity to a second polypeptide comprising SEQ ID NO: 2, or fragments or analogs thereof;
(b) a polypeptide having at least 95% identity to a second polypeptide comprising SEQ ID NO: 2, or fragments or analogs thereof;
(c) a polypeptide comprising SEQ ID NO: 2, or fragments or analogs thereof;
(d) a polypeptide capable of raising antibodies having binding specificity for a polypeptide comprising SEQ ID NO: 2, or fragments or analogs thereof;
(e) an epitope bearing portion of a polypeptide comprising SEQ ID NO: 2, or fragments or analogs thereof;
(f) the polypeptide of (a), (b), (c), (d), (e) or (f) wherein the N-terminal Met residue is deleted;
(g) the polypeptide of (a), (b), (c), (d), (e) or (f) wherein the secretory amino acid sequence is deleted.

According to one aspect, the present invention provides an isolated polypeptide comprising a polypeptide chosen from:
(a) a polypeptide having at least 70% identity to a second polypeptide comprising SEQ ID NO: 2;
(b) a polypeptide having at least 95% identity to a second polypeptide comprising SEQ ID NO: 2;
(c) a polypeptide comprising SEQ ID NO: 2;
(d) a polypeptide capable of raising antibodies having binding specificity for a polypeptide comprising SEQ ID NO: 2;
(e) an epitope bearing portion of a polypeptide comprising SEQ ID NO: 2;
(f) the polypeptide of (a), (b), (c), (d), (e) or (f) wherein the N-terminal Met residue is deleted;
(g) the polypeptide of (a), (b), (c), (d), (e) or (f) wherein the secretory amino acid sequence is deleted.

Those skilled in the art will appreciate that the invention includes DNA molecules, i.e. polynucleotides and their complementary sequences that encode analogs such as mutants, variants, homologues and derivatives of such polypeptides, as described herein in the present patent application. The invention also includes RNA molecules corresponding to the DNA molecules of the invention. In addition to the DNA and RNA molecules, the invention includes the corresponding polypeptides and monospecific antibodies that specifically bind to such polypeptides.

In a further embodiment, the polypeptides in accordance with the present invention are antigenic.

In a further embodiment, the polypeptides in accordance with the present invention are immunogenic.

In a further embodiment, the polypeptides in accordance with the present invention can elicit an immune response in a host.

In a further embodiment, the present invention also relates to polypeptides which are able to raise antibodies having binding specificity to the polypeptides of the present invention as defined above.

An antibody that "has binding specificity" is an antibody that recognizes and binds the selected polypeptide but which does not substantially recognize and bind other molecules in a sample, e.g., a biological sample. Specific binding can be measured using an ELISA assay in which the selected polypeptide is used as an antigen.

In accordance with the present invention, "protection" in the biological studies is defined by a significant increase in the survival curve, rate or period. Statistical analysis using the Log rank test to compare survival curves, and Fisher exact test to compare survival rates and numbers of days to death, respectively, might be useful to calculate P values and determine whether the difference between the two groups is statistically significant. P values of 0.05 are regarded as not significant.

In an additional aspect of the invention there are provided antigenic/immunogenic fragments of the polypeptides of the invention, or of analogs thereof.

The fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a polypeptide or analog thereof as described herein. The present invention further provides fragments having at least 10 contiguous amino acid residues from the polypeptide sequences of the present invention. In one embodiment, at least 15 contiguous amino acid residues. In one embodiment, at least 20 contiguous amino acid residues.

The key issue, once again, is that the fragment retains the antigenic/immunogenic properties.

The skilled person will appreciate that analogs of the polypeptides of the invention will also find use in the context of the present invention, i.e. as antigenic/immunogenic material. Thus, for instance proteins or polypeptides which include one or more additions, deletions, substitutions or the like are encompassed by the present invention.

As used herein, "fragments", "analogs" or "derivatives" of the polypeptides of the invention include those polypeptides in which one or more of the amino acid residues are substituted with a conserved or non-conserved amino acid residue (preferably conserved) and which may be natural or unnatural. In one embodiment, derivatives and analogs of polypeptides of the invention will have about 70% identity with those sequences illustrated in the figures or fragments thereof. That is, 70% of the residues are the same. In a further embodiment, polypeptides will have greater than 80% identity. In a further embodiment, polypeptides will have greater than 85% identity. In a further embodiment, polypeptides will have greater than 90% identity. In a further embodiment, polypeptides will have greater than 95% identity. In a further embodiment, polypeptides will have greater than 99% identity. In a further embodiment, analogs of polypeptides of the invention will have fewer than about 20 amino acid residue substitutions, modifications or deletions and more preferably less than 10.

These substitutions are those having a minimal influence on the secondary structure and hydropathic nature of the polypeptide. Preferred substitutions are those known in the art as conserved, i.e. the substituted residues share physical or chemical properties such as hydrophobicity, size, charge or functional groups. These include substitutions such as those described by Dayhoff, M. in Atlas of Protein Sequence and Structure 5, 1978 and by Argos, P. in EMBO J. 8, 779-785, 1989. For example, amino acids, either natural or unnatural, belonging to one of the following groups represent conservative changes:

ala, pro, gly, gln, asn, ser, thr, val;
cys, ser, tyr, thr;
val, ile, leu, met, ala, phe;
lys, arg, orn, his;
and phe, tyr, trp, his.

The preferred substitutions also include substitutions of D-enantiomers for the corresponding L-amino acids.

In an alternative approach, the analogs of the polypeptides of the invention comprise the substitutions disclosed in FIG. 3.

In an alternative approach, the analogs could be fusion proteins, incorporating moieties which render purification easier, for example by effectively tagging the desired polypeptide. It may be necessary to remove the "tag" or it may be the case that the fusion polypeptide itself retains sufficient antigenicity to be useful.

The percentage of homology is defined as the sum of the percentage of identity plus the percentage of similarity or conservation of amino acid type.

In one embodiment, analogs of polypeptides of the invention will have about 70% identity with those sequences illustrated in the figures or fragments thereof. That is, 70% of the residues are the same. In a further embodiment, polypeptides will have greater than 75% homology. In a further embodiment, polypeptides will have 30 greater than 80% homology. In a further embodiment, polypeptides will have greater than 85% homology. In a further embodiment, polypeptides will have greater than 90% homology. In a further embodiment, polypeptides will have greater than 95% homology. In a further embodiment, polypeptides will have greater than 99% homology. In a further embodiment, analogs of polypeptides of the invention will have fewer than about 20 amino acid residue substitutions, modifications or deletions and more preferably less than 10.

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

In an alternative approach, the analogs or derivatives could be fusion polypeptides, incorporating moieties which render purification easier, for example by effectively tagging the desired protein or polypeptide, it may be necessary to remove the "tag" or it may be the case that the fusion polypeptide itself retains sufficient antigenicity to be useful.

It is well known that is possible to screen an antigenic polypeptide to identify epitopic regions, i.e. those regions which are responsible for the polypeptide's antigenicity or immunogenicity. Methods for carrying out such screening are well known in the art. Thus, the fragments of the present invention should include one or more such epitopic regions or be sufficiently similar to such regions to retain their antigenic/immunogenic properties.

Thus, for fragments according to the present invention the degree of identity is perhaps irrelevant, since they may be 100% identical to a particular part of a polypeptide, analog as described herein.

Thus, what is important for analogs, derivatives and fragments is that they possess at least a degree of the antigenicity/immunogenicity of the protein or polypeptide from which they are derived.

Also included are polypeptides which have fused thereto other compounds which alter the polypeptides biological or pharmacological properties i.e. polyethylene glycol (PEG) to increase half-life; leader or secretory amino acid sequences for ease of purification; prepro- and pro- sequences; and (poly)saccharides.

Furthermore, in those situations where amino acid regions are found to be polymorphic, it may be desirable to vary one or more particular amino acids to more effectively mimic the different epitopes of the different *streptococcus* strains.

Moreover, the polypeptides of the present invention can be modified by terminal —NH$_2$ acylation (eg. by acetylation, or thioglycolic acid amidation, terminal carboxy amidation, e.g. with ammonia or methylamine) to provide stability, increased hydrophobicity for linking or binding to a support or other molecule.

Also contemplated are hetero and homo polypeptide multimers of the polypeptide fragments and analogues. These polymeric forms include, for example, one or more polypeptides that have been cross-linked with cross-linkers such as avidin/biotin, gluteraldehyde or dimethylsuperimidate. Such polymeric forms also include polypeptides containing two or more tandem or inverted contiguous sequences, produced from multicistronic mRNAs generated by recombinant DNA technology. In a further embodiment, the present invention also relates to chimeric polypeptides which comprise one or more polypeptides or fragments or analogs thereof as defined in the figures of the present application.

In a further embodiment, the present invention also relates to chimeric polypeptides comprising two or more polypeptides having a sequence chosen from SEQ ID NO: 2, or fragments or analogs thereof; provided that the polypeptides are linked as to formed a chimeric polypeptide.

In a further embodiment, the present invention also relates to chimeric polypeptides comprising two or more polypeptides having a sequence chosen from SEQ ID NO: 2 provided that the polypeptides are linked as to formed a chimeric polypeptide.

Preferably, a fragment, analog or derivative of a polypeptide of the invention will comprise at least one antigenic region i.e. at least one epitope.

In order to achieve the formation of antigenic polymers (i.e. synthetic multimers), polypeptides may be utilized having bishaloacetyl groups, nitroarylhalides, or the like, where the reagents being specific for thio groups. Therefore, the link between two mercapto groups of the different polypeptides may be a single bond or may be composed of a linking group of at least two, typically at least four, and not more than 16, but usually not more than about 14 carbon atoms.

In a particular embodiment, polypeptide fragments and analogs of the invention do not contain a methionine (Met) starting residue. Preferably, polypeptides will not incorporate a leader or secretory sequence (signal sequence). The signal portion of a polypeptide of the invention may be determined according to established molecular biological techniques. In general, the polypeptide of interest may be isolated from a streptococcal culture and subsequently sequenced to determine the initial residue of the mature protein and therefore the sequence of the mature polypeptide.

It is understood that polypeptides can be produced and/or used without their start codon (methionine or valine) and/or without their leader peptide to favor production and purification of recombinant polypeptides. It is known that cloning genes without sequences encoding leader peptides will restrict the polypeptides to the cytoplasm of *E. coli* and will facilitate their recovery (Glick, B. R. and Pasternak, J. J. (1998) Manipulation of gene expression in prokaryotes. In "Molecular biotechnology: Principles and applications of recombinant DNA", 2nd edition, ASM Press, Washington D.C., p. 109-143).

According to another aspect of the invention, there are also provided (i) a composition of matter containing a polypeptide of the invention, together with a carrier, diluent or adjuvant; (ii) a pharmaceutical composition comprising a polypeptide of the invention and a carrier, diluent or adjuvant; (iii) a vaccine comprising a polypeptide of the invention and a carrier, diluent or adjuvant; (iv) a method for inducing an immune response against *Streptococcus*, in a host, by administering to the host, an immunogenically effective amount of a polypeptide of the invention to elicit an immune response, e.g., a protective immune response to *Streptococcus*; and particularly, (v) a method for preventing and/or treating a *Streptococcus* infection, by administering a prophylactic or therapeutic amount of a polypeptide of the invention to a host in need.

According to another aspect of the invention, there are also provided (i) a composition of matter containing a polynucleotide of the invention, together with a carrier, diluent or adjuvant; (ii) a pharmaceutical composition comprising a polynucleotide of the invention and a carrier, diluent or adjuvant; (iii) a method for inducing an immune response against *Streptococcus*, in a host, by administering to the host, an immunogenically effective amount of a polynucleotide of the invention to elicit an immune response, e.g., a protective immune response to *Streptococcus*; and particularly, (iv) a method for preventing and/or treating a *Streptococcus* infection, by administering a prophylactic or therapeutic amount of a polynucleotide of the invention to a host in need.

Before immunization, the polypeptides of the invention can also be coupled or conjugated to carrier proteins such as tetanus toxin, diphtheria toxin, hepatitis B virus surface antigen, poliomyelitis virus VP1 antigen or any other viral or bacterial toxin or antigen or any suitable proteins to stimulate the development of a stronger immune response. This coupling or conjugation can be done chemically or genetically. A more detailed description of peptide-carrier conjugation is available in Van Regenmortel, M. H. V., Briand J. P., Muller S., Plaué S., <<Synthetic Polypeptides as antigens>>in Laboratory Techniques in Biochemistry and Molecular Biology, Vol. 19 (ed.) Burdou, R. H. & Van Knippenberg P. H. (1988), Elsevier N. Y.

According to another aspect, there are provided pharmaceutical compositions comprising one or more Streptococcal polypeptides of the invention in a mixture with a pharmaceutically acceptable adjuvant. Suitable adjuvants include (1) oil-in-water emulsion formulations such as MF59®, SAF™, Ribi™; (2) Freund's complete or incomplete adjuvant; (3) salts, e.g., AlK(SO$_4$)$_2$, AlNa(SO$_4$)$_2$, AlNH$_4$(SO$_4$)$_2$, Al(OH)$_3$, AlPO$_4$, silica, kaolin; (4) saponin derivatives such as STIMULON® or particles generated therefrom such as ISCOMs (immunostimulating complexes) (5) cytokines such as interleukins, interferons, macrophage colony stimulating factor (M-CSF), tumor necrosis factor (TNF); (6) other substances such as carbon polynucleotides, e.g., poly IC and poly AU, detoxified cholera toxin (CTB) and *E. coli* heat labile toxin for induction of mucosal immunity. A more detailed description of adjuvant is available in a review by M. Z. I Khan et al. in Pharmaceutical Research, vol. 11, No. 1 (1994) pp 2-11, and also in another review by Gupta et al., in Vaccine, Vol. 13, No. 14, pp 1263-1276 (1995) and in WO 99/24578, which are herein incorporated by reference. Preferred adjuvants include QuilA™ (an adjuvant containing saponins from bark of *Quillaja saponaria*), QS21 ™ (purified fraction of Saponin extracted from *Quillaja saponaria*), ALHYDROGEL® (an aluminum hydroxide (hydrated alumina) adjuvant), and Adjuphos™ (an aluminum phosphate adjuvant).

Pharmaceutical compositions of the invention may be administered parenterally by injection, rapid infusion, nasopharyngeal absorption, dermoabsorption, or buccal or oral.

Pharmaceutical compositions of the invention are used for the treatment or prophylaxis of streptococcal infection and/or diseases and symptoms mediated by streptococcal infection as described in P. R. Murray (Ed, in chief), E. J. Baron, M. A.

Pfaller, F. C. Tenover and R. H. Yolken. Manual of Clinical Microbiology, ASM Press, Washington, D.C. sixth edition, 1995, 1482p which are herein incorporated by reference. In one embodiment, pharmaceutical compositions of the present invention are used for the prophylaxis or treatment of pharyngitis, erysipelas and impetigo, scarlet fever, and invasive diseases such as bacteremia and necrotizing fasciitis and also toxic shock. In one embodiment, pharmaceutical compositions of the invention are used for the prophylaxis or treatment of *Streptococcus* infection and/or diseases and symptoms mediated by *Streptococcus* infection, in particular group A *Streptococcus* (*Streptococcus pyogenes*), group B *Streptococcus* (GBS or *S. agalactiae*), *S. pneumoniae*, *S. dysgalactiae*, *S. uberis*, *S. nocardia* as well as *Staphylococcus aureus*. In a further embodiment, the *Streptococcus* infection is *S. pyogenes*.

In a further embodiment, the invention provides a method for prophylaxis or treatment of *Streptococcus* infection in a host susceptible to *Streptococcus* infection comprising administering to said host a therapeutic or prophylactic amount of a composition of the invention.

As used in the present application, the term "host" includes mammals. In a further embodiment, the mammal is human.

In a particular embodiment, pharmaceutical compositions are administered to those hosts at risk of *streptococcus* infection such as infants, elderly and immunocompromised hosts.

Pharmaceutical compositions are preferably in unit dosage form of about 0.001 to 100 µg/kg (antigen/body weight) and more preferably 0.01 to 10 µg/kg and most preferably 0.1 to 1 µg/kg 1 to 3 times with an interval of about 1 to 6 week intervals between immunizations.

Pharmaceutical compositions are preferably in unit dosage form of about 0.1 µg to 10 mg and more preferably 1 µg to 1 mg and most preferably 10 to 100 µg 1 to 3 times with an interval of about 1 to 6 week intervals between immunizations.

According to another aspect, there are provided polynucleotides encoding polypeptides characterized by the amino acid sequence comprising SEQ ID NO: 2 or fragments or analogs thereof.

In one embodiment, polynucleotides are those illustrated in SEQ ID No: 1 which may include the open reading frames (ORF), encoding the polypeptides of the invention.

It will be appreciated that the polynucleotide sequences illustrated in the figures may be altered with degenerate codons yet still encode the polypeptides of the invention. Accordingly the present invention further provides polynucleotides which hybridize to the polynucleotide sequences herein above described (or the complement sequences thereof) having 50% identity between sequences. In one embodiment, at least 70% identity between sequences. In one embodiment, at least 75% identity between sequences. In one embodiment, at least 80% identity between sequences. In one embodiment, at least 85% identity between sequences. In one embodiment, at least 90% identity between sequences. In a further embodiment, polynucleotides are hybridizable under stringent conditions i.e. having at least 95% identity. In a further embodiment, more than 97% identity.

Suitable stringent conditions for hybridization can be readily determined by one of skilled in the art (see for example Sambrook et al., (1989) Molecular cloning : A Laboratory Manual, $2^{nd}$ ed, Cold Spring Harbor, N.Y.; Current Protocols in Molecular Biology, (1999) Edited by Ausubel F. M. et al., John Wiley & Sons, Inc., N.Y.).

In a further embodiment, the present invention provides polynucleotides that hybridize under stringent conditions to either (a) a DNA sequence encoding a polypeptide or
(b) the complement of a DNA sequence encoding a polypeptide;

wherein said polypeptide comprises SEQ ID NO: 2, or fragments or analogs thereof.

In a further embodiment, the present invention provides polynucleotides that hybridize under stringent conditions to either (a) a DNA sequence encoding a polypeptide or
(b) the complement of a DNA sequence encoding a polypeptide;

wherein said polypeptide comprises SEQ ID NO: 2.

In a further embodiment, the present invention provides polynucleotides that hybridize under stringent conditions to either (a) a DNA sequence encoding a polypeptide or
(b) the complement of a DNA sequence encoding a polypeptide;

wherein said polypeptide comprises at least 10 contiguous amino acid residues from a polypeptide comprising SEQ ID NO: 2, or fragments or analogs thereof.

In a further embodiment, the present invention provides polynucleotides that hybridize under stringent conditions to either (a) a DNA sequence encoding a polypeptide or
(b) the complement of a DNA sequence encoding a polypeptide;

wherein said polypeptide comprises at least 10 contiguous amino acid residues from a polypeptide comprising SEQ ID NO: 2.

In a further embodiment, polynucleotides are those encoding 30 polypeptides of the invention illustrated in SEQ ID NO: 2 or fragments or analogs thereof.

In a further embodiment, polynucleotides are those illustrated in SEQ ID NO: 1 encoding polypeptides of the invention or fragments or analogs thereof.

In a further embodiment, polynucleotides are those encoding polypeptides of the invention illustrated in SEQ ID NO: 2.

In a further embodiment, polynucleotides are those illustrated in SEQ ID NO: 1 encoding polypeptides of the invention.

As will be readily appreciated by one skilled in the art, polynucleotides include both DNA and RNA.

The present invention also includes polynucleotides complementary to the polynucleotides described in the present application.

In a further aspect, polynucleotides encoding polypeptides of the invention, or fragments, analogs or derivatives thereof, may be used in a DNA immunization method. That is, they can be incorporated into a vector which is replicable and expressible upon injection thereby producing the antigenic polypeptide in vivo. For example polynucleotides may be incorporated into a plasmid vector under the control of the CMV promoter which is functional in eukaryotic cells. Preferably the vector is injected intramuscularly.

According to another aspect, there is provided a process for producing polypeptides of the invention by recombinant techniques by expressing a polynucleotide encoding said polypeptide in a host cell and recovering the expressed polypeptide product. Alternatively, the polypeptides can be produced according to established synthetic chemical techniques i.e. solution phase or solid phase synthesis of oligopeptides which are ligated to produce the full polypeptide (block ligation).

General methods for obtention and evaluation of polynucleotides and polypeptides are described in the following references: Sambrook et al, Molecular Cloning: A Laboratory Manual, 2nd ed, Cold Spring Harbor, N.Y., 1989; Current Protocols in Molecular Biology, Edited by Ausubel F. M. et al., John Wiley and Sons, Inc. New York; PCR Cloning Protocols, from Molecular Cloning to Genetic Engineering, Edited by White B. A., Humana Press, Totowa, N.J., 1997, 490 pages; Protein Purification, Principles and Practices, Scopes R. K., Springer-Verlag, New York, 3rd Edition, 1993, 380 pages; Current Protocols in Immunology, Edited by Coligan J. E. et al., John Wiley & Sons Inc., New York which are herein incorporated by reference.

For recombinant production, host cells are transfected with vectors which encode the polypeptide, and then cultured in a nutrient media modified as appropriate for activating promoters, selecting transformants or amplifying the genes. Suitable vectors are those that are viable and replicable in the chosen host and include chromosomal, non-chromosomal and synthetic DNA sequences e.g. bacterial plasmids, phage DNA, baculovirus, yeast plasmids, vectors derived from combinations of plasmids and phage DNA. The polypeptide sequence may be incorporated in the vector at the appropriate site using restriction enzymes such that it is operably linked to an expression control region comprising a promoter, ribosome binding site (consensus region or Shine-Dalgarno sequence), and optionally an operator (control element) One can select individual components of the expression control region that are appropriate for a given host and vector according to established molecular biology principles (Sambrook et al, Molecular Cloning: A Laboratory Manual, 2nd ed, Cold Spring Harbor, N.Y., 1989; Current Protocols in Molecular Biology, Edited by Ausubel F. M. et al., John Wiley and Sons, Inc. New York incorporated herein by reference). Suitable promoters include but are not limited to LTR or SV40 promoter, *E. coli* lac, tac or trp promoters and the phage lambda $P_L$ promoter. Vectors will preferably incorporate an origin of replication as well as selection markers i.e. ampicilin resistance gene. Suitable bacterial vectors include pET, pQE70, pQE60, pQE-9, pD10 phagescript, psiX174, pbluescript SK, pbsks, pNH8A, pNH16a, pNH18A, pNH46A, ptrc99a, pKK223-3, pKK233-3, pDR540, pRIT5 and eukaryotic vectors pBlueBacIII, pWLNEO, pSV2CAT, pOG44, pXT1, pSG, pSVK3, pBPV, pMSG and pSVL. Host cells may be bacterial i.e. *E. coli, Bacillus subtilis, Streptomyces*; fungal i.e. *Aspergillus niger, Aspergillus nidulins*; yeast i.e. *Saccharomyces* or eukaryotic i.e. CHO, COS.

Upon expression of the polypeptide in culture, cells are typically harvested by centrifugation then disrupted by physical or chemical means (if the expressed polypeptide is not secreted into the media) and the resulting crude extract retained to isolate the polypeptide of interest. Purification of the polypeptide from culture media or lysate may be achieved by established techniques depending on the properties of the polypeptide i.e. using ammonium sulfate or ethanol precipitation, acid extraction, anion or cation exchange chromatography, phosphocellulose chromatography, hydrophobic interaction chromatography, hydroxylapatite chromatography and lectin chromatography. Final purification may be achieved using HPLC.

The polypeptides may be expressed with or without a leader or secretion sequence. In the former case the leader may be removed using post-translational processing (see U.S. Pat. No. 4,431,739; U.S. Pat. No. 4,425,437; and U.S. Pat. No. 4,338,397 incorporated herein by reference) or be chemically removed subsequent to purifying the expressed polypeptide.

According to a further aspect, the streptococcal polypeptides of the invention may be used in a diagnostic test for *Streptococcus* infection, in particular *S. pyogenes* infection. Several diagnostic methods are possible, for example detecting *Streptococcus* organism in a biological sample, the following procedure may be followed:
 a) obtaining a biological sample from a host;
 b) incubating an antibody or fragment thereof reactive with a *Streptococcus* polypeptide of the invention with the biological sample to form a mixture; and
 c) detecting specifically bound antibody or bound fragment in the mixture which indicates the presence of *Streptococcus*.

Alternatively, a method for the detection of antibody specific to a *Streptococcus* antigen in a biological sample containing or suspected of containing said antibody may be performed as follows:
 a) obtaining a biological sample from a host;
 b) incubating one or more *Streptococcus* polypeptides of the invention or fragments thereof with the biological sample to form a mixture; and
 c) detecting specifically bound antigen or bound fragment in the mixture which indicates the presence of antibody specific to *Streptococcus*.

One of skill in the art will recognize that this diagnostic test may take several forms, including an immunological test such as an enzyme-linked immunosorbent assay (ELISA), a radioimmunoassay or a latex agglutination assay, essentially to determine whether antibodies specific for the protein are present in an organism.

The DNA sequences encoding polypeptides of the invention may also be used to design DNA probes for use in detecting the presence of *Streptococcus* in a biological sample suspected of containing such bacteria. The detection method of this invention comprises:
 a) obtaining the biological sample from a host;
 b) incubating one or more DNA probes having a DNA sequence encoding a polypeptide of the invention or fragments thereof with the biological sample to form a mixture; and
 c) detecting specifically bound DNA probe in the mixture which indicates the presence of *Streptococcus* bacteria.

The DNA probes of this invention may also be used for detecting circulating *Streptococcus* i.e. *S. pyogenes* nucleic acids in a sample, for example using a polymerase chain reaction, as a method of diagnosing *Streptococcus* infections. The probe may be synthesized using conventional techniques and may be immobilized on a solid phase, or may be labelled with a detectable label. A preferred DNA probe for this application is an oligomer having a sequence complementary to at least about 6 contiguous nucleotides of the *S. pyogenes* polypeptides of the invention.

Another diagnostic method for the detection of *Streptococcus* in a host comprises:
 a) labelling an antibody reactive with a polypeptide of the invention or fragment thereof with a detectable label;
 b) administering the labelled antibody or labelled fragment to the host; and
 c) detecting specifically bound labelled antibody or labelled fragment in the host which indicates the presence of *Streptococcus*.

According to one aspect, the present invention provides the use of an antibody for treatment and/or prophylaxis of streptococcal infections.

A further aspect of the invention is the use of the *Streptococcus* polypeptides of the invention as immunogens for the production of specific antibodies for the diagnosis and in particular the treatment of *streptococcus* infection. Suitable antibodies may be determined using appropriate screening methods, for example by measuring the ability of a particular antibody to passively protect against *streptococcus* infection in a test model. One example of an animal model is the mouse model described in the examples herein. The antibody may be a whole antibody or an antigen-binding fragment thereof and may belong to any immunoglobulin class. The antibody or fragment may be of animal origin, specifically of mammalian origin and more specifically of murine, rat or human origin. It may be a natural antibody or a fragment thereof, or if desired, a recombinant antibody or antibody fragment. The term recombinant antibody or antibody fragment means antibody or antibody fragment which was produced using molecular biology techniques. The antibody or antibody fragments may be polyclonal, or preferably monoclonal. It may be specific for a number of epitopes associated with the *S. pyogenes* polypeptides but is preferably specific for one.

A further aspect of the invention is the use of the antibodies directed to the polypeptides of the invention for passive immunization. One could use the antibodies described in the present application.

A further aspect of the invention is a method for immunization; whereby an antibody raised by a polypeptide of the invention is administered to a host in an amount sufficient to provide a passive immunization.

In a further embodiment, the invention provides the use of a pharmaceutical composition in the manufacture of a medicament for the prophylactic or therapeutic treatment of streptococcal infection.

In a further embodiment, the invention provides a kit comprising a polypeptide of the invention for detection or diagnosis of streptococcal infection.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLE 1

This example illustrates the cloning and molecular characteristics of BVH-P7 gene and corresponding polypeptide.

The coding region of *S. pyogenes* BVH-P7 (SEQ ID NO: 1) gene was amplified by PCR (ROBOCYCLER® Gradient 96 Temperature cycler, Stratagene®, LaJolla, Calif.) from genomic DNA of serotype M1 *S. pyogenes* strain ATCC700294 using the following oligonucleotide primers that contained base extensions for the addition of restriction sites NdeI (CATATG) and NotI (GCGGCCGC): DMAR293 and DMAR294, which are presented in Table 1. PCR products were purified from agarose gel using a QIA® quick gel extraction kit from QIAGEN® following the manufacturer's instructions (Chatsworth, Calif.), and digested with NdeI and NotI (Amersham Pharmacia Biotech Inc, Baie d'Urfé, Canada). The pET-21b(+) vector (NOVAGEN®, Madison, Wis.) was digested with NdeI and NotI and purified from agarose gel using a QIA® quick gel extraction kit from QIAGEN® (Chatsworth, Calif.) The NdeI-NotI PCR products were ligated to the NdeI-NotI pET-21b(+) expression vector. The ligated products were transformed into *E. coli* strain DH5• [φ80dlacZΔM15 Δ(lacZYA-argF)U169 endA1 recA1 hsdR17($r_K$–$m_K$+) deoR thi-1 supE44 λgyrA96 relA1] (Gibco BRL, Gaithersburg, Md.) according to the method of Simanis (Hanahan, D. DNA Cloning, 1985, D. M. Glover (ed), pp. 109-135). Recombinant pET-21b(+) plasmid (rpET21b(+)) containing BVH-P7 gene was purified using a QIAGEN® plasmid kit (Chatsworth, Calif.) and DNA insert was sequenced (Taq Dye Deoxy Terminator Cycle Sequencing kit, ABI, Foster City, Calif.).

TABLE 1

Oligonucleotide primers used for PCR amplifications of *S. pyogenes* BVH-P7 gene

| Genes | Primers I.D. (SEQ ID NO) | Restriction site | Vector | Sequence |
|---|---|---|---|---|
| BVH-P7 | DMAR293 (3) | NdeI | pET21b | 5'-GTAGTCACCCACCATATGGAAGTTTTTAG-3' (SEQ ID NO: 9) |
| BVH-P7 | DMAR294 (4) | NotI | pET21b | 5'-TTTTTTCTTTGCGGCCGCAGTTATTAGT-3' (SEQ ID NO: 10) |
| BVH-P7 | DMAR480a (5) | BamHI | pCMV-GH | 5'-GGGGATCCCACCCACAATCAGG-3' (SEQ ID NO: 11) |
| BVH-P7 | DMAR481a (6) | SalI | pCMV-GH | 5'-GGTTGTCGACAGTAAAGCAACGCTAGTG-3' (SEQ ID NO: 12) |

It was determined that the 3027-hp including a stop codon (TAA) open reading frame (ORF) of BVH-P7 encodes a 1008 amino-acid-residues polypeptide with a predicted pI of 6.18 and a predicted molecular mass of 111,494.44 Da. Analysis of the predicted amino acid residues sequence (SEQ ID NO :2) using the PSORTII software (Real World Computing Partnership suggested) the existence of a 21 amino acid residues signal peptide (MKKHLKTVALTLTTVSVVTHN) (SEQ ID NO: 13), which ends with a cleavage site situated between an asparagine and a glutamine residues. Analysis of the amino-acid-residues sequence revealed the presence of a cell wall anchoring motif (LPXTGX) (SEQ ID NO: 14) located between residues 974 and 981.

To confirm the presence by PCR amplification of BVH-P7 (SEQ ID NO :1) gene, the following 4 serologically distinct *S. pyogenes* strains were used: the serotype M1 *S. pyogenes* strain ATCC700294 and the serotype M3 *S. pyogenes* strain ATCC12384 were obtained from the American Type Culture Collection (Manassas, Va.); the serotype M6 *S. pyogenes* SPY67 clinical isolate was provided by the Centre de recherche en infectiologie du Centre hospitalier de l'université

Laval, Sainte-Foy; and S. pyogenes strain B514 which was initially isolated from a mouse was provided by Susan Hollingshead, from University of Ala., Birmingham. The E. coli strain XL1-Blue MRF' was used in these experiments as negative control. Chromosomal DNA was isolated from each S. pyogenes strain as previously described (Jayarao B M et al. 1991. J. Clin. Microbiol. 29:2774-2778). BVH-P7 (SEQ ID NO:1) gene was amplified by PCR (Robocycler Gradient 96 Temperature cycler, Stratagene, LaJolla, Calif.) from the genomic DNA purified from the 4 S. pyogenes strains, and the control E. coli strain using the oligonucleotide primers DMAR293 and DMAR294 (Table 1). PCR was performed with 30 cycles of 45 sec at 95° C., 45 sec at 50° C. and 2 min at 72° C. and a final elongation period of 7 min at 72° C. The PCR products were size fractionated in 1% agarose gels and were visualized by ethidium bromide staining. The results of these PCR amplifications are presented in Table 2. The analysis of the amplification products revealed that BVH-P7 (SEQ ID NO:1) gene was present in the genome of all of the 4 S. pyogenes strains tested. No such product was detected when the control E. coli DNA was submitted to identical PCR amplifications with these oligonucleotide primers.

TABLE 2

Identification of S. pyogenes BVH-P7 gene by PCR amplification in the genome of four serologically distinct S. pyogenes strains

| Strain Identification | Identification of BVH-P7 gene |
|---|---|
| ATCC700294 (M1) | + |
| ATCC12384 (M3) | + |
| SPY67 (M6) | + |
| B514* | + |
| E. coil XL1 Blue MRF' | − |

*Mouse isolate

EXAMPLE 2

This example illustrates the cloning of S. pyogenes BVH-P7 gene in CMV plasmid pCMV-GH.

The DNA coding region of S. pyogenes protein was inserted in phase downstream of a human growth hormone (hGH) gene which was under the transcriptional control of the cytomegalovirus (CMV) promotor in the plasmid vector pCMV-GH (Tang et al., Nature, 1992, 356 :152). The CMV promotor is a non functional plasmid in E. coli cells but active upon administration of the plasmid in eukaryotic cells. The vector also incorporated the ampicillin resistance gene.

The coding regions of BVH-P7 (SEQ ID NO: 1) gene without its leader peptide region was amplified by PCR (ROBOCYCLER® Gradient 96 Temperature cycler, STRATAGENE®, Lajolla, Calif.) from genomic DNA of serotype M1 *S. pyogenes* strain ATCC700294 using oligonucleotide primers DMAR480a and DMAR481a that contained base extensions for the addition of restriction sites BamHI (GGATCC) and SalI (GTCGAC) which are described in Table 1. The PCR products were purified from agarose gel using a QIA® quick gel extraction kit from QIAGEN® (Chatsworth, Calif.), digested with restriction enzymes (Amersham Pharmacia Biotech Inc, Baie d'Urfé, Canada). The pCMV-GH vector (Laboratory of Dr. Stephen A. Johnston, Department of Biochemistry, The University of Texas, Dallas, Tex.) was digested with BamHI and SalI and purified from agarose gel using the QIA® quick gel extraction kit from QIAGEN® (Chatsworth, Calif.). The BamHI-SalI DNA fragment was ligated to the BamHI-SalI-pCMV-GH vector to create the hGH-BVH-P7 fusion protein under the control of the CMV promoter. The ligated product was transformed into *E. coli* strain DH5• [$\phi$80dlacZ$\Delta$M15 $\Delta$(lacZYA-argF)U169 endA1 recA1 hsdR17($r_K$–$m_K$+) deoR thi-1 supE44 $\lambda$gyrA96 relA1] (Gibco BRL, Gaithersburg, Md.) according to the method of Simanis (Hanahan, D. DNA Cloning, 1985, D. M. Glover (ed), pp. 109-135). The recombinant pCMV plasmid was purified using a QIAGEN® plasmid kit (Chatsworth, Calif.) and the nucleotide sequence of the DNA insert was verified by DNA sequencing.

EXAMPLE 3

This example illustrates the use of DNA to elicit an immune response to *S. pyogenes BVH-P7* protein antigen. Groups of 8 female BALB/c mice (Charles River, St-Constant, Québec, Canada) were immunized by intramuscular injection of 100 μl three times at two- or three-week intervals with 50 μg of recombinant pCMV-GH encoding BVH-P7 (SEQ ID NO: 1) gene in presence of 50 μg of granulocyte-macrophage colony-stimulating factor (GM-CSF)-expressing plasmid pCMV-GH-GM-CSF (Laboratory of Dr. Stephen A. Johnston, Department of Biochemistry, The University of Texas, Dallas, Tex.). As control, groups of mice were injected with 50 μg of pCMV-GH in presence of 50 μg of pCMV-GH-GM-CSF. Blood samples were collected from the orbital sinus prior to each immunization and seven days following the third injection and serum antibody responses were determined by ELISA using the BVH-P7 His-tagged labeled *S. pyogenes* recombinant protein as coating antigen. The production and purification of this BVH-P7 His-tagged labeled *S. pyogenes* recombinant protein is presented in Example 4.

EXAMPLE 4

This example illustrates the production and purification of *S. pyogenes* BVH-P7 recombinant protein.

The recombinant pET-21b(+) plasmid with BVH-P7 (SEQ ID NO: 1) gene was used to transform by electroporation (Gene Pulser II apparatus, BIO-RAD® Labs, Mississauga, Canada) *E. coli* strain Tuner (DE3) ($F^-$ompT hsd$S_B$ ($r^-_B m^-_B$) gal dcm lacYI (DE3)) (NOVAGEN®, Madison, Wis.). In this strain of *E. coli*, the T7 promotor controlling expression of the recombinant protein is specifically recognized by the T7 RNA polymerase (present on the $\lambda$DE3 prophage) whose gene is under the control of the lac promotor which is inducible by isopropyl-β-d-thio-galactopyranoside (IPTG). The transformants Tuner (DE3)/rpET21 (+) were grown at 37° C. with agitation at 250 rpm in LB broth (peptone 10 g/L, yeast extract 5 g/L, NaCl 10 g/L) containing 100 μg of carbenicillin (Sigma-Aldrich Canada Ltd., Oakville, Canada) per ml until the $A_{600}$ reached a value of 0.6. In order to induce the production of BVH-P7 His-tagged *S. pyogenes* recombinant protein, the cells were incubated for 3 additional hours in the presence of IPTG at a final concentration of 0.1 mM. Induced cells from a 500 ml culture were pelleted by centrifugation and frozen at −70° C.

The purification of the BVH-P7 His-tagged recombinant protein from the non-soluble fraction of IPTG-induced Tuner (DE3)/rpET21b(+) was done by affinity chromatography based on the properties of the His●Tag sequence (6 consecutive histidine residues) to bind to divalent cations ($Ni^{2+}$) immobilized on the His●Bind metal chelation resin. Briefly, the pelleted cells obtained from a 500 mL culture induced with IPTG was resuspended in lysis buffer (20 mM Tris, 500 mM NaCl, 10 mM imidazole, pH 7.9) containing 6M Guanidine-HCl, sonicated and centrifuged at 12,000×g for 20 min to remove debris. The supernatant was incubated with Ni-NTA agarose resin (QIAGEN®, Mississauga, Ontario, Canada) for 45 min at 4° C. The BVH-P7 His-tagged *S. pyogenes* recombinant protein was eluted from the resin with a solution containing 6M Guanidine-HCl and 250 mM imidazole-500 mM NaCl-20 mM Tris, pH 7.9. The removal of the salt and imidazole from the samples was done by dialysis against 10 mM Tris and 0.9% NaCl, pH 7.9 overnight at 4° C. The amount of recombinant protein was estimated by MicroBCA (Pierce, Rockford, Ill).

EXAMPLE 5

This example illustrates the reactivity of the BVH-P7 His-tagged *S. pyogenes* recombinant protein with human sera and sera collected from mice after immunization with *S. pyogenes* antigenic preparations.

As shown in Table 3, purified His-tagged BVH-P7 recombinant protein was recognized in immunoblots by the antibodies present in the pool of normal sera. This is an important result since it clearly indicates that human which are normally in contact with *S. pyogenes* do develop antibodies that are specific to that protein. These particular human antibodies might be implicated in the protection against *S. pyogenes* infection. In addition, immunoblots also revealed that sera collected from mice immunized with *S. pyogenes* antigenic preparations enriched membrane proteins which protected mice against lethal challenge also developed antibodies that recognized BVH-P7 His-tagged recombinant protein. This result indicates that this protein was present in *S. pyogenes* antigenic preparation that protected mice against infection and that this streptococcal protein induced antibodies that reacted with the corresponding His-tagged recombinant protein.

TABLE 3

Reactivity in immunoblots of human sera and sera collected from mice after immunization with *S. pyogenes* antigenic preparations with BVH-P7 His-tagged recombinant protein.

| Purified recombinant protein I.D.[1] | Apparent molecular weight (kDa)[2] | Reactivity in immunoblots with | |
|---|---|---|---|
| | | Human sera[3] | Mouse sera[4] |
| BVH-P7 | 110 | + | + |

[1]BVH-P7 His-tagged recombinant protein produced and purified as described in Example 7 was used to perform the immunoblots.
[2]Molecular weight of the BVH-P7 His-tagged recombinant protein was estimated after SDS-PAGE.
[3]Two sera collected from healthy human volunteers were pooled together and diluted 1/500 to perform the immunoblots.
[4]Mouse sera collected after immunization with *S. pyogenes* antigenic preparations enriched membrane proteins were pooled and diluted 1/500 to perform the immunoblots. These mice were protected against a lethal *S. pyogenes* challenge.

EXAMPLE 6

This example illustrates the accessibility to antibodies of the *S. pyogenes* BVH-P7 protein at the surface of intact streptococcal cells.

Bacteria were grown in Tood Hewitt (TH) broth (Difco Laboratories, Detroit, Mich.) with 0.5% Yeast extract (Difco Laboratories) and 0.5% peptone extract (Merck, Darmstadt, Germany) at 37° C. in a 8% $CO_2$ atmosphere to give an $OD_{490\,nm}$ of 0.600 (~$10^8$ CFU/ml). Dilutions of anti-BVH-P7 or control sera were then added and allowed to bind to the cells, which were incubated for 2 h at 4° C. Samples were washed 4 times in blocking buffer [phosphate-buffered saline (PBS) containing 2% bovine serum albumin (BSA)], and then 1 ml of goat fluorescein (FITC)-conjugated anti-mouse IgG+IgM diluted in blocking buffer was added. After an additional incubation of 60 min at room temperature, samples were washed 4 times in blocking buffer and fixed with 0.25% formaldehyde in PBS buffer for 18-24 h at 4° C. Cells were washed 2 times in PBS buffer and resuspended in 500 μl of PBS buffer. Cells were kept in the dark at 4° C. until analyzed by flow cytometry (Epics® XL; Beckman Coulter, Inc.). Ten thousands intact *S. pyogenes* cells were analyzed per sample and the results were expressed as percentage of labeled cells and fluorescence index. The fluorescence index was calculated as the median fluorescence value obtained after labeling the streptococcal cells with an immune serum divided by the fluorescence value obtained for a control mouse serum. A fluorescence value of 1 indicated that there was no binding of antibodies at the surface of intact streptococcal cells.

Sera collected from eight mice immunized with BVH-P7 His-tagged recombinant protein were analyzed by cytofluorometry and the results are presented in Table 4. All of the sera collected from mice immunized with purified BVH-P7 His-tagged protein contained BVH-P7-specific antibodies that efficiently recognized their corresponding surface exposed epitopes on the heterologous (ATCC12384; serotype M3) *S. pyogenes* strain tested. The fluorescence index varied from 10 to 18. It was determined that more than 97% of the 10,000 *S. pyogenes* cells analyzed were labeled with the antibodies present in the BVH-P7 specific anti-sera. These sera were also pooled and reacted with the following *S. pyogenes* strains: serotype M1 *S. pyogenes* strain ATCC700294, serotype M3 and serotype M18 *S. pyogenes* strain ATCC12357 were obtained from the American Type Culture Collection (Manassas, Va.); the serotype M6 *S. pyogenes* SPY69 and M2 *S. pyogenes* SPY68 clinical isolates were provided by the Centre de recherche en infectiologie du Centre hospitalier de l'université Laval, Sainte-Foy. The BVH-P7-specific antibodies present in the pool of sera collected after immunization with the purified His-tagged recombinant BVH-P7 protein attached at the bacterial surface of each of these streptococcal strains with fluorescence index between 4 up to 9. On the contrary, no labeling of the streptococcal cells were noted when pools of sera collected from unimmunized or sham-immunized mice were used. These observations clearly demonstrate that the BVH-P7 protein is accessible at the surface where it can be easily recognized by antibodies. Anti-*S. pyogenes* antibodies were shown to play an important role in the protection against *S. pyogenes* infection.

TABLE 4

Evaluation of the attachment of BVH-P7-specific antibodies at the surface of intact cells of *S. pyogenes* ATCC12384 strain (serotype M3).

| Serum Identification | Fluorescence Index[2] | % of labeled cells[3] |
|---|---|---|
| S1[1] | 11 | 97 |
| S2 | 11 | 97 |
| S3 | 13 | 98 |
| S4 | 16 | 99 |
| S5 | 10 | 97 |
| S6 | 12 | 97 |
| S7 | 13 | 98 |
| S8 | 18 | 99 |

TABLE 4-continued

Evaluation of the attachment of BVH-P7-specific antibodies at the surface of intact cells of *S. pyogenes* ATCC12384 strain (serotype M3).

| Serum Identification | Fluorescence Index[2] | % of labeled cells[3] |
|---|---|---|
| Pool of negative control sera[4] | 1 | 9 |
| Positive control serum[5] | 12 | 98 |

[1]The mice S1 to S8 were injected subcutaneously three times at three-week intervals with 20 µg of purified BVH-P7 recombinant protein mixed with 10 µg of QuilA ™ adjuvant (Cedarlane Laboratories, Hornby, Canada). The sera were diluted 1/50.
[2]The fluorescence index was calculated as the median fluorescence value obtained after labeling the streptococcal cells with an immune serum divided by the fluorescence value obtained for a control mouse serum. A fluorescence value of 1 indicated that there was no binding of antibodies at the surface of intact streptococcal cells.
[3]% of streptococcal labeled cells out of the 10,000 cells analyzed.
[4]Sera collected from unimmunized or sham-immunized mice were pooled diluted 1/50 and used as negative controls for this assay.
[5]Serum obtained from a mouse immunized with 20 µg of purified streptococcal recombinant M protein, a well known surface protein, was diluted 1/200 and was used as a positive control for the assay.

The mice S1 to S8 were injected subcutaneously three times at three-week intervals with 20 µg of purified BVH-P7 recombinant protein mixed with 10 µg of QuilA™ adjuvant (Cedarlane Laboratories, Hornby, Canada). The sera were diluted (1/50).

EXAMPLE 7

This example illustrates the protection against fatal *S. pyogenes* infection induced by passive immunization of mice with rabbit hyper-immune sera.

New Zealand rabbits (Charles River laboratories, St-Constant, Canada) are injected subcutaneously at multiple sites with 50 µg and 100 µg of the BVH-P7 His-tagged recombinant protein that is produced and purified as described in Example 4 and adsorbed to ALHYDROGEL® adjuvant (SUPERFOS® Biosector a/s). Rabbits are immunized three times at three-week intervals with the BVH-P7 His-tagged recombinant protein. Blood samples are collected three weeks after the third injection. The antibodies present in the serum are purified by precipitation using 40% saturated ammonium sulfate. Groups of 10 female CD-1 mice (Charles River) are injected intravenously with 500 µl of purified serum collected from rabbits immunized with the BVH-P7 His-tagged recombinant protein, or rabbits immunized with an unrelated control recombinant protein. Eighteen hours later the mice are challenged with approximately $2 \times 10^7$ CFU of the type 3 *S. pyogenes* strain ATCC12384. Samples of the *S. pyogenes* challenge inoculum are plated on blood agar plates to determine the CFU and to verify the challenge dose. Deaths are recorded for a period of 5 days.

EXAMPLE 8

This example illustrates the protection of mice against fatal *S. pyogenes* infection induced by immunization with purified recombinant BVH-P7 protein.

Groups of 8 female Balb/c mice (Charles River, St-Constant, Québec, Canada) were immunized subcutaneously three times at two-week intervals with 20 μg of affinity purified BVH-P7 His-tagged recombinant protein in presence of 10 μg of QuilA™ adjuvant (Cedarlane Laboratories Ltd, Hornby, Canada) or, as control, with QuilA™ adjuvant alone in PBS. Blood samples were collected from the orbital sinus on day 1, 14 and 28 prior to each immunization and two weeks (day 42) following the third injection. One week later the mice were challenged with approximately $3\times10^6$ CFU of the type 3 *S. pyogenes* strain ATCC 12384. Samples of the *S. pyogenes* challenge inoculum were plated on blood agar plates to determine the CFU and to verify the challenge dose. Deaths were recorded for a period of 7 days. Four of eight mice immunized with purified recombinant BVH-P7 protein were protected against the lethal challenge, compared to only 12% (1/8) of mice which received the adjuvant alone (Table 1).

TABLE 5

Ability of recombinant BVH-P7 protein to elicit protection against GAS strain ATCC 12384 (Type 3).

| Immunogen | No. mice surviving | % survival |
|---|---|---|
| 20 μg BVH-P7 + 10% QuilA | 4/8 | 50 |
| QuilA adjuvant alone in PBS | 1/8 | 12 |

What is claimed is:

1. An isolated polypeptide comprising an amino acid sequence at least 95% identical to the full-length amino acid sequence set forth in SEQ ID NO:2, wherein the isolated polypeptide is capable of eliciting an immune response to *Streptococcus pyogenes*, and wherein the isolated polypeptide is capable of eliciting an antibody that specifically binds to a BVH-P7 polypeptide that consists of the amino acid sequence set forth in SEQ ID NO:2.

2. The isolated polypeptide of claim 1 comprising the amino acid sequence set forth in SEQ ID NO:2.

3. An isolated polypeptide comprising the amino acid sequence set forth in SEQ ID NO:2 from which the N-terminal methionine residue is deleted.

4. An isolated polypeptide comprising the amino acid sequence set forth in SEQ ID NO:2 which lacks the signal peptide consisting of the amino acid sequence at positions 1-21 of SEQ ID NO:2.

5. A pharmaceutical composition comprising the isolated polypeptide of any one of claims 1-4 and a pharmaceutically acceptable carrier, diluent or adjuvant.

6. A vaccine composition comprising the isolated polypeptide of any one of claims 1-4 and a pharmaceutically acceptable carrier, diluent or adjuvant.

* * * * *

SEQUENCE LISTING

<160> NUMBER OF SEQ ID NOS: 14

<210> SEQ ID NO 1
<211> LENGTH: 3027
<212> TYPE: DNA
<213> ORGANISM: Streptococcus pyogenes

<400> SEQUENCE: 1

```
atgaagaaac atcttaaaac agttgccttg accctcacta cagtatcggt agtcacccac      60
aatcaggaag tttttagttt agtcaaagag ccaattctta aacaaactca agcttcttca     120
tcgatttctg gcgctgacta cgcagaaagt agcggtaaaa gcaagttaaa gattaatgaa     180
acttctggcc ctgttgatga tacagtcact gacttatttt cggataaacg tactactcct     240
gaaaaaataa aagataatct tgctaaaggt ccgagagaac aagagttaaa ggcagtaaca     300
```

-continued

```
gagaatacag aatcagaaaa gcagatcact tctggatctc aactagaaca atcaaaagag    360 tctcttctt taaataaaac agtgccatca acgtctaatt gggagatttg tgattttatt     420
actaagggga ataccettgt tggtctttca aaatcaggtg ttgaaaagtt atctcaaact    480
gatcatctcg tattgcctag tcaagcagca gatggaactc aattgataca agtagctagt   540
tttgctttta ctccagataa aaagacggca attgcagaat ataccagtag ggctggagaa   600 aatgggaaa taagccaact agatgtggat ggaaaagaaa ttattaacga aggtgaggtt    660
tttaattctt atctactaaa gaaggtaaca atcccaactg ttataaaca tattggtcaa    720 gatgcttttg tggacaataa gaatattgct gaggttaatc ttcctgaaag cctcgagact   780
atttctgact atgcttttgc tcacctagct ttgaaacaga tcgatttgcc agataattta   840
aaagcgattg gagaattagc ttttttgat aatcaaatta caggtaaact ttctttgcca    900
cgtcagttaa tgcgattagc agaacgtgct tttaaatcaa accatatcaa acaattgag    960 tttagaggaa atagtctaaa agtgataggg gaagctagtt ttcaagataa tgatctgagt  1020
caactaatgc tacctgacgg tcttgaaaaa atagaatcag aagcttttac aggaaatcca  1080
ggagatgatc actacaataa ccgtgttgtt ttgtggacaa atctggaaa aaatccttct   1140 ggtcttgcta ctgaaaatac ctatgttaat cctgataagt cactatggca ggaaagtcct  1200
gagattgatt atactaaatg gttagaggaa gattttacct atcaaaaaaa tagtgttaca  1260 ggttttcaa ataaaggctt acaaaaagta aaacgtaata aaaacttaga aattccaaaa   1320
cagcacaatg gtgttactat tactgaaatt ggtgataatg cttttcgcaa tgttgatttt  1380
caaaataaaa ctttacgtaa atatgatttg gaagaagtaa agcttccctc aactattcgg  1440
aaaataggtg cttttgcttt tcaatctaat aacttgaaat cttttgaagc aagtgacgat  1500
ttagaagaga ttaaagaggg agcctttatg aataatcgta ttgaaacctt ggaattaaaa  1560
gataaattag ttactattgg tgatgcggct ttccatatta atcatattta tgccattgtt  1620
cttccagaat ctgtacaaga aatagggcgt tcagcatttc ggcaaaatgg tgcaaataat  1680 cttatttta tgggaagtaa ggttaagacc ttaggtgaga tggcattttt atcaaataga   1740
cttgaacatc tggatctttc tgagcaaaaa cagttaacag agattcctgt tcaagccttt  1800
tcagacaatg ccttgaaaga agtattatta ccagcatcac tgaaaacgat tcgaaagaa  1860 gccttcaaaa agaatcattt aaaacaactg gaagtggcat ctgccttgtc ccatattgct  1920
tttaatgctt tagatgataa tgatggtgat gaacaatttg ataataaagt ggttgttaaa  1980
acgcatcata attcctacgc actagcagat ggtgagcatt ttatcgttga tccagataag  2040
ttatcttcta caatagtaga ccttgaaaag atttaaaac taatcgaagg tttagattat   2100
tctacattac gtcagactac tcaaactcag tttagagaca tgactactgc aggtaaagcg  2160
ttgttgtcaa atctaaccct ccgacaagga gaaaaacaaa aattccttca agaagcacaa  2220
tttttccttg gccgcgttga tttggataaa gccatagcta agctgagaa ggctttagtg    2280 accaagaagg caacaaagaa tggtcagttg cttgaaagaa gtattaacaa agcggtatta  2340
gcttataata atagcgctat taaaaagct aatgttaagc gcttggaaaa agagttagac   2400 tgctaacag gattagttga gggaaaagga ccattagcgc aagctacaat ggtacaagga   2460
gtttatttat taaagacgcc tttgccattg ccagaatatt atatcggatt gaacgtttat  2520
tttgacaagt ctggaaaatt gatttatgca cttgatatga gtgatactat ggcgaggga   2580 caaaaagacg cttatggtaa tcctatatta aatgttgacg aggataatga aggttatcat  2640
gccttggcag ttgccacttt agctgattat gaggggctcg acatcaaaac aattttaaat  2700
```

-continued

```
agtaagctta gtcaattaac atctattcgt caggtaccga ctgcagccta tcatagagcc    2760
ggtattttcc aagctatcca aaatgcagcg gcagaagcag agcagttatt gcctaaacca    2820
ggtacgcact ctgagaagtc aagctcaagt gaatctgcta actctaaaga tagaggattg    2880
caatcaaacc caaaaacgaa tagaggacga cactctgcaa tattgcctag acagggtca     2940 aaaggcagct ttgtctatgg aatcttaggt tacactagcg ttgctttact gtcactaata    3000
actgctataa aaagaaaaa atattaa                                          3027
```

<210> SEQ ID NO 2
<211> LENGTH: 1008
<212> TYPE: PRT
<213> ORGANISM: Streptococcus pyogenes

<400> SEQUENCE: 2

```
Met Lys Lys His Leu Lys Thr Val Ala Leu Thr Leu Thr Thr Val Ser
  1               5                  10                  15

Val Val Thr His Asn Gln Glu Val Phe Ser Leu Val Lys Glu Pro Ile
             20                  25                  30

Leu Lys Gln Thr Gln Ala Ser Ser Ile Ser Gly Ala Asp Tyr Ala
         35                  40                  45

Glu Ser Ser Gly Lys Ser Lys Leu Lys Ile Asn Glu Thr Ser Gly Pro
     50                  55                  60

Val Asp Asp Thr Val Thr Asp Leu Phe Ser Asp Lys Arg Thr Thr Pro
 65                  70                  75                  80

Glu Lys Ile Lys Asp Asn Leu Ala Lys Gly Pro Arg Glu Gln Glu Leu
                 85                  90                  95

Lys Ala Val Thr Glu Asn Thr Glu Ser Glu Lys Gln Ile Thr Ser Gly
            100                 105                 110

Ser Gln Leu Glu Gln Ser Lys Glu Ser Leu Ser Leu Asn Lys Thr Val
        115                 120                 125

Pro Ser Thr Ser Asn Trp Glu Ile Cys Asp Phe Ile Thr Lys Gly Asn
    130                 135                 140

Thr Leu Val Gly Leu Ser Lys Ser Gly Val Glu Lys Leu Ser Gln Thr
145                 150                 155                 160

Asp His Leu Val Leu Pro Ser Gln Ala Ala Asp Gly Thr Gln Leu Ile
                165                 170                 175

Gln Val Ala Ser Phe Ala Phe Thr Pro Asp Lys Lys Thr Ala Ile Ala
            180                 185                 190

Glu Tyr Thr Ser Arg Ala Gly Glu Asn Gly Glu Ile Ser Gln Leu Asp
        195                 200                 205

Val Asp Gly Lys Glu Ile Ile Asn Glu Gly Glu Val Phe Asn Ser Tyr
    210                 215                 220

Leu Leu Lys Lys Val Thr Ile Pro Thr Gly Tyr Lys His Ile Gly Gln
225                 230                 235                 240

Asp Ala Phe Val Asp Asn Lys Asn Ile Ala Glu Val Asn Leu Pro Glu
                245                 250                 255

Ser Leu Glu Thr Ile Ser Asp Tyr Ala Phe Ala His Leu Ala Leu Lys
            260                 265                 270

Gln Ile Asp Leu Pro Asp Asn Leu Lys Ala Ile Gly Glu Leu Ala Phe
        275                 280                 285

Phe Asp Asn Gln Ile Thr Gly Lys Leu Ser Leu Pro Arg Gln Leu Met
    290                 295                 300

Arg Leu Ala Glu Arg Ala Phe Lys Ser Asn His Ile Lys Thr Ile Glu
```

-continued

```
            305                 310                 315                 320
        Phe Arg Gly Asn Ser Leu Lys Val Ile Gly Glu Ala Ser Phe Gln Asp
                        325                 330                 335

Asn Asp Leu Ser Gln Leu Met Leu Pro Asp Gly Leu Glu Lys Ile Glu
                        340                 345                 350

Ser Glu Ala Phe Thr Gly Asn Pro Gly Asp His Tyr Asn Asn Arg
                        355                 360                 365

Val Val Leu Trp Thr Lys Ser Gly Lys Asn Pro Ser Gly Leu Ala Thr
                        370                 375                 380

Glu Asn Thr Tyr Val Asn Pro Asp Lys Ser Leu Trp Gln Glu Ser Pro
        385                 390                 395                 400

Glu Ile Asp Tyr Thr Lys Trp Leu Glu Glu Asp Phe Thr Tyr Gln Lys
                        405                 410                 415

Asn Ser Val Thr Gly Phe Ser Asn Lys Gly Leu Gln Lys Val Lys Arg
                        420                 425                 430

Asn Lys Asn Leu Glu Ile Pro Lys Gln His Asn Gly Val Thr Ile Thr
                        435                 440                 445

Glu Ile Gly Asp Asn Ala Phe Arg Asn Val Asp Phe Gln Asn Lys Thr
                        450                 455                 460

Leu Arg Lys Tyr Asp Leu Glu Val Lys Leu Pro Ser Thr Ile Arg
        465                 470                 475                 480

Lys Ile Gly Ala Phe Ala Phe Gln Ser Asn Asn Leu Lys Ser Phe Glu
                        485                 490                 495

Ala Ser Asp Asp Leu Glu Glu Ile Lys Glu Gly Ala Phe Met Asn Asn
                        500                 505                 510

Arg Ile Glu Thr Leu Glu Leu Lys Asp Lys Leu Val Thr Ile Gly Asp
                        515                 520                 525

Ala Ala Phe His Ile Asn His Ile Tyr Ala Ile Val Leu Pro Glu Ser
                        530                 535                 540

Val Gln Glu Ile Gly Arg Ser Ala Phe Arg Gln Asn Gly Ala Asn Asn
        545                 550                 555                 560

Leu Ile Phe Met Gly Ser Lys Val Lys Thr Leu Gly Glu Met Ala Phe
                        565                 570                 575

Leu Ser Asn Arg Leu Glu His Leu Asp Leu Ser Glu Gln Lys Gln Leu
                        580                 585                 590

Thr Glu Ile Pro Val Gln Ala Phe Ser Asp Asn Ala Leu Lys Glu Val
                        595                 600                 605

Leu Leu Pro Ala Ser Leu Lys Thr Ile Arg Glu Glu Ala Phe Lys Lys
                        610                 615                 620

Asn His Leu Lys Gln Leu Glu Val Ala Ser Ala Leu Ser His Ile Ala
        625                 630                 635                 640

Phe Asn Ala Leu Asp Asp Asn Asp Gly Asp Glu Gln Phe Asp Asn Lys
                        645                 650                 655

Val Val Val Lys Thr His His Asn Ser Tyr Ala Leu Ala Asp Gly Glu
                        660                 665                 670

His Phe Ile Val Asp Pro Asp Lys Leu Ser Ser Thr Ile Val Asp Leu
                        675                 680                 685

Glu Lys Ile Leu Lys Leu Ile Glu Gly Leu Asp Tyr Ser Thr Leu Arg
                        690                 695                 700

Gln Thr Thr Gln Thr Gln Phe Arg Asp Met Thr Thr Ala Gly Lys Ala
        705                 710                 715                 720

Leu Leu Ser Lys Ser Asn Leu Arg Gln Gly Glu Lys Gln Lys Phe Leu
                        725                 730                 735
```

Gln Glu Ala Gln Phe Phe Leu Gly Arg Val Asp Leu Asp Lys Ala Ile
            740                 745                 750

Ala Lys Ala Glu Lys Ala Leu Val Thr Lys Lys Ala Thr Lys Asn Gly
            755                 760                 765

Gln Leu Leu Glu Arg Ser Ile Asn Lys Ala Val Leu Ala Tyr Asn Asn
            770                 775                 780

Ser Ala Ile Lys Lys Ala Asn Val Lys Arg Leu Glu Lys Glu Leu Asp
785                 790                 795                 800

Leu Leu Thr Gly Leu Val Glu Gly Lys Gly Pro Leu Ala Gln Ala Thr
                805                 810                 815

Met Val Gln Gly Val Tyr Leu Leu Lys Thr Pro Leu Pro Leu Pro Glu
            820                 825                 830

Tyr Tyr Ile Gly Leu Asn Val Tyr Phe Asp Lys Ser Gly Lys Leu Ile
            835                 840                 845

Tyr Ala Leu Asp Met Ser Asp Thr Ile Gly Glu Gly Gln Lys Asp Ala
            850                 855                 860

Tyr Gly Asn Pro Ile Leu Asn Val Asp Glu Asp Asn Glu Gly Tyr His
865                 870                 875                 880

Ala Leu Ala Val Ala Thr Leu Ala Asp Tyr Glu Gly Leu Asp Ile Lys
                885                 890                 895

Thr Ile Leu Asn Ser Lys Leu Ser Gln Leu Thr Ser Ile Arg Gln Val
            900                 905                 910

Pro Thr Ala Ala Tyr His Arg Ala Gly Ile Phe Gln Ala Ile Gln Asn
            915                 920                 925

Ala Ala Ala Glu Ala Glu Gln Leu Leu Pro Lys Pro Gly Thr His Ser
930                 935                 940

Glu Lys Ser Ser Ser Ser Glu Ser Ala Asn Ser Lys Asp Arg Gly Leu
945                 950                 955                 960

Gln Ser Asn Pro Lys Thr Asn Arg Gly Arg His Ser Ala Ile Leu Pro
                965                 970                 975

Arg Thr Gly Ser Lys Gly Ser Phe Val Tyr Gly Ile Leu Gly Tyr Thr
            980                 985                 990

Ser Val Ala Leu Leu Ser Leu Ile Thr Ala Ile Lys Lys Lys Lys Tyr
            995                 1000                1005

<210> SEQ ID NO 3
<211> LENGTH: 951
<212> TYPE: PRT
<213> ORGANISM: Streptococcus pyogenes

<400> SEQUENCE: 3

Asp Tyr Ala Glu Ser Ser Gly Lys Ser Lys Leu Lys Ile Asn Glu Thr
1               5                   10                  15

Ser Gly Pro Val Asp Asp Thr Val Thr Asp Leu Phe Ser Asp Lys Arg
            20                  25                  30

Thr Thr Pro Glu Lys Ile Lys Asp Asn Leu Ala Lys Gly Pro Arg Glu
        35                  40                  45

Gln Glu Leu Lys Ala Val Thr Glu Asn Thr Glu Ser Glu Lys Gln Ile
    50                  55                  60

Thr Ser Gly Ser Gln Leu Glu Gln Ser Lys Glu Ser Leu Ser Leu Asn
65                  70                  75                  80

Lys Arg Val Pro Ser Thr Ser Asn Trp Glu Ile Cys Asp Phe Ile Thr
                85                  90                  95

Lys Gly Asn Thr Leu Val Gly Leu Ser Lys Ser Gly Val Glu Lys Leu

-continued

```
                100                 105                 110
Ser Gln Thr Asp His Leu Val Leu Pro Ser Gln Ala Asp Gly Thr
            115                 120                 125
Gln Leu Ile Gln Val Ala Ser Phe Ala Phe Thr Pro Asp Lys Lys Thr
        130                 135                 140
Ala Ile Ala Glu Tyr Thr Ser Arg Ala Gly Glu Asn Gly Glu Ile Ser
145                 150                 155                 160
Gln Leu Asp Val Asp Gly Lys Glu Ile Ile Asn Glu Gly Glu Val Phe
                165                 170                 175
Asn Ser Tyr Leu Leu Lys Lys Val Thr Ile Pro Thr Gly Tyr Lys His
            180                 185                 190
Ile Gly Gln Asp Ala Phe Val Asp Asn Lys Asn Ile Ala Glu Val Asn
        195                 200                 205
Leu Pro Glu Ser Leu Glu Thr Ile Ser Asp Tyr Ala Phe Ala His Leu
210                 215                 220
Ala Leu Lys Gln Ile Asp Leu Pro Asp Asn Leu Lys Ala Ile Gly Glu
225                 230                 235                 240
Leu Ala Phe Phe Asp Asn Gln Ile Thr Gly Lys Leu Ser Leu Pro Arg
                245                 250                 255
Gln Leu Met Arg Leu Ala Glu Arg Ala Phe Lys Ser Asn His Ile Lys
            260                 265                 270
Thr Ile Glu Phe Arg Gly Asn Ser Leu Lys Val Ile Gly Glu Ala Ser
        275                 280                 285
Phe Gln Asp Asn Asp Leu Ser Gln Leu Met Leu Pro Asp Gly Leu Glu
290                 295                 300
Lys Ile Glu Ser Glu Ala Phe Thr Gly Asn Pro Gly Asp Asp His Tyr
305                 310                 315                 320
Asn Asn Arg Val Val Leu Trp Thr Lys Ser Gly Lys Asn Pro Tyr Gly
                325                 330                 335
Leu Ala Thr Glu Asn Thr Tyr Val Asn Pro Asp Lys Ser Leu Trp Gln
            340                 345                 350
Glu Ser Pro Glu Ile Asp Tyr Thr Lys Trp Leu Glu Glu Asp Phe Thr
        355                 360                 365
Tyr Gln Lys Asn Ser Val Thr Gly Phe Ser Ser Lys Gly Leu Gln Lys
370                 375                 380
Val Lys Arg Asn Lys Asn Leu Glu Ile Pro Lys Gln His Asn Gly Val
385                 390                 395                 400
Thr Ile Thr Glu Ile Gly Asp Asn Ala Phe Arg Asn Val Asp Phe Gln
                405                 410                 415
Asn Lys Thr Leu Arg Lys Tyr Asp Leu Glu Glu Val Lys Leu Pro Ser
            420                 425                 430
Thr Ile Arg Lys Ile Gly Ala Phe Ala Phe Gln Ser Asn Asn Leu Lys
        435                 440                 445
Ser Phe Glu Ala Ser Asp Asp Leu Glu Glu Ile Lys Glu Gly Ala Phe
450                 455                 460
Met Asn Asn Arg Ile Glu Thr Leu Glu Leu Lys Asp Lys Leu Val Thr
465                 470                 475                 480
Ile Gly Asp Ala Ala Phe His Ile Asn His Ile Tyr Ala Ile Val Leu
                485                 490                 495
Pro Glu Ser Val Gln Glu Ile Gly Arg Ser Ala Phe Arg Gln Asn Gly
            500                 505                 510
Ala Asn Asn Leu Ile Phe Met Gly Ser Lys Val Lys Thr Ile Gly Glu
        515                 520                 525
```

```
Met Ala Phe Leu Ser Asn Arg Leu Glu His Leu Asp Leu Ser Glu Gln
530                 535                 540

Lys Gln Leu Thr Glu Ile Pro Val Gln Ala Phe Ser Asp Asn Ala Leu
545                 550                 555                 560

Lys Glu Val Leu Leu Pro Ala Ser Leu Lys Thr Ile Arg Glu Glu Ala
                565                 570                 575

Phe Lys Lys Asn His Leu Lys Gln Leu Glu Val Ala Ser Ala Leu Ser
                580                 585                 590

His Ile Ala Phe Asn Ala Leu Asp Asp Asn Asp Gly Asp Glu Gln Phe
                595                 600                 605

Asp Asn Lys Val Val Lys Thr His His Asn Ser Tyr Ala Leu Ala
610                 615                 620

Asp Gly Glu His Phe Ile Val Asp Pro Asp Lys Leu Ser Ser Thr Met
625                 630                 635                 640

Val Asp Leu Glu Lys Ile Leu Lys Leu Ile Glu Gly Leu Asp Tyr Ser
                645                 650                 655

Thr Leu Arg Gln Thr Thr Gln Thr Gln Phe Arg Asp Met Thr Thr Ala
                660                 665                 670

Gly Lys Ala Leu Leu Ser Lys Ser Lys Leu Arg Gln Gly Glu Lys Gln
                675                 680                 685

Lys Phe Leu Gln Glu Ala Gln Phe Phe Leu Gly Arg Val Asp Leu Asp
                690                 695                 700

Lys Ala Ile Ala Lys Ala Glu Lys Ala Leu Val Thr Lys Lys Ala Thr
705                 710                 715                 720

Lys Asn Gly Gln Leu Leu Gly Arg Ser Ile Asn Lys Ala Val Leu Ala
                725                 730                 735

Tyr Asn Asn Ser Ala Ile Lys Lys Ala Asn Val Lys Arg Leu Glu Lys
                740                 745                 750

Glu Leu Asp Leu Leu Thr Gly Leu Val Glu Gly Lys Gly Pro Leu Ala
                755                 760                 765

Gln Ala Thr Met Val Gln Gly Val Tyr Leu Leu Lys Thr Pro Leu Pro
770                 775                 780

Leu Pro Glu Tyr Tyr Ile Gly Leu Asn Val Tyr Phe Asp Lys Ser Gly
785                 790                 795                 800

Lys Leu Ile Tyr Ala Leu Asp Met Ser Asp Thr Ile Gly Glu Gly Gln
                805                 810                 815

Lys Asp Ala Tyr Gly Asn Pro Ile Leu Asn Val Asp Glu Asp Asn Glu
                820                 825                 830

Gly Tyr His Ala Leu Ala Val Ala Thr Leu Ala Asp Tyr Glu Gly Leu
                835                 840                 845

Asp Ile Lys Thr Ile Leu Asn Ser Lys Leu Ser Gln Leu Thr Ser Ile
850                 855                 860

Arg Gln Val Pro Thr Ala Ala Tyr His Arg Ala Gly Ile Phe Gln Ala
865                 870                 875                 880

Ile Gln Asn Ala Ala Ala Glu Ala Glu Gln Leu Leu Pro Lys Pro Gly
                885                 890                 895

Thr His Ser Glu Lys Ser Ser Ser Glu Ser Ala Asn Ser Lys Asp
                900                 905                 910

Arg Gly Leu Gln Ser Asn Pro Lys Thr Asn Arg Gly Arg His Ser Ala
                915                 920                 925

Ile Leu Pro Arg Thr Gly Ser Lys Gly Ser Phe Val Tyr Gly Ile Leu
930                 935                 940
```

```
Gly Tyr Thr Ser Val Ala Leu
945                 950

<210> SEQ ID NO 4
<211> LENGTH: 970
<212> TYPE: PRT
<213> ORGANISM: Streptococcus pyogenes

<400> SEQUENCE: 4

Leu Val Lys Glu Pro Ile Leu Lys Gln Thr Gln Ala Ser Ser Ser Ile
 1               5                  10                  15

Ser Gly Ala Asp Tyr Ala Glu Ser Ser Gly Lys Ser Lys Leu Lys Ile
            20                  25                  30

Asn Glu Thr Ser Gly Pro Val Asp Asp Thr Val Thr Asp Leu Phe Ser
        35                  40                  45

Asp Lys Arg Thr Thr Pro Glu Lys Ile Lys Asp Asn Leu Ala Lys Gly
    50                  55                  60

Pro Arg Glu Gln Glu Leu Lys Ala Val Thr Gln Asn Thr Glu Ser Glu
65                  70                  75                  80

Lys Gln Ile Asn Ser Gly Ser Gln Leu Glu Gln Ser Lys Glu Ser Leu
                85                  90                  95

Ser Leu Asn Lys Arg Val Pro Ser Thr Ser Asn Trp Glu Ile Cys Asp
            100                 105                 110

Phe Ile Thr Lys Gly Asn Thr Leu Val Gly Leu Ser Lys Ser Gly Val
        115                 120                 125

Glu Lys Leu Ser Gln Thr Asp His Leu Val Leu Pro Ser Gln Ala Ala
    130                 135                 140

Asp Gly Thr Gln Leu Ile Gln Val Ala Ser Phe Ala Phe Thr Pro Asp
145                 150                 155                 160

Lys Lys Thr Ala Ile Ala Glu Tyr Thr Ser Arg Ala Gly Glu Asn Gly
                165                 170                 175

Glu Ile Ser Gln Leu Asp Val Asp Gly Lys Glu Ile Ile Asn Glu Gly
            180                 185                 190

Glu Val Phe Asn Ser Tyr Leu Leu Lys Lys Val Thr Ile Pro Thr Gly
        195                 200                 205

Tyr Lys His Ile Gly Gln Asp Ala Phe Val Asp Asn Lys Asn Ile Ala
    210                 215                 220

Glu Val Asn Leu Pro Glu Ser Leu Glu Thr Ile Ser Asp Tyr Ala Phe
225                 230                 235                 240

Ala His Leu Ala Leu Lys Gln Ile Asp Leu Pro Asp Asn Leu Lys Ala
                245                 250                 255

Ile Gly Glu Leu Ala Phe Phe Asp Asn Gln Ile Thr Gly Lys Leu Ser
            260                 265                 270

Leu Pro Arg Gln Leu Met Arg Leu Ala Glu Arg Ala Phe Lys Ser Asn
        275                 280                 285

His Ile Lys Thr Ile Glu Phe Arg Gly Asn Ser Leu Lys Val Ile Gly
    290                 295                 300

Glu Ala Ser Phe Gln Asp Asn Asp Leu Ser Gln Leu Met Leu Pro Asp
305                 310                 315                 320

Gly Leu Glu Lys Ile Glu Ser Glu Ala Phe Thr Gly Asn Pro Gly Asp
                325                 330                 335

Asp His Tyr Asn Asn Arg Val Val Leu Trp Thr Lys Ser Gly Lys Asn
            340                 345                 350

Pro Tyr Gly Leu Ala Thr Glu Asn Thr Tyr Val Asn Pro Asp Lys Ser
        355                 360                 365
```

```
Leu Trp Gln Glu Ser Pro Glu Ile Asp Tyr Thr Lys Trp Leu Glu Glu
    370                 375                 380

Asp Phe Thr Tyr Gln Lys Asn Ser Val Thr Gly Phe Ser Ser Lys Gly
385                 390                 395                 400

Leu Gln Lys Val Lys Arg Asn Lys Asn Leu Glu Ile Pro Lys Gln His
                405                 410                 415

Asn Gly Val Thr Ile Thr Glu Ile Gly Asp Asn Ala Phe Arg Asn Val
            420                 425                 430

Asp Phe Gln Asn Lys Thr Leu Arg Lys Tyr Asp Leu Glu Glu Val Lys
        435                 440                 445

Leu Pro Ser Thr Ile Arg Lys Ile Gly Ala Phe Ala Phe Gln Ser Asn
    450                 455                 460

Asn Leu Lys Ser Phe Glu Ala Ser Asp Asp Leu Glu Glu Ile Lys Glu
465                 470                 475                 480

Gly Ala Phe Met Asn Asn Arg Ile Glu Thr Leu Glu Leu Lys Asp Lys
                485                 490                 495

Leu Val Thr Ile Gly Asp Ala Ala Phe His Ile Asn His Ile Tyr Ala
            500                 505                 510

Ile Val Leu Pro Glu Ser Val Gln Glu Ile Gly Arg Ser Ala Phe Arg
        515                 520                 525

Gln Asn Gly Ala Asn Asn Leu Ile Phe Met Gly Ser Lys Val Lys Thr
    530                 535                 540

Leu Gly Glu Met Ala Phe Leu Ser Asn Arg Leu Glu His Leu Asp Leu
545                 550                 555                 560

Ser Glu Gln Lys Gln Leu Thr Glu Ile Pro Val Gln Ala Phe Ser Asp
                565                 570                 575

Asn Ala Leu Lys Glu Val Leu Leu Pro Ala Ser Leu Lys Thr Ile Arg
            580                 585                 590

Glu Glu Ala Phe Lys Lys Asn His Leu Lys Gln Leu Glu Val Ala Ser
        595                 600                 605

Ala Leu Ser His Ile Ala Phe Asn Ala Leu Asp Asp Asn Asp Gly Asp
    610                 615                 620

Glu Gln Phe Asp Asn Lys Val Val Lys Thr His His Asn Ser Tyr
625                 630                 635                 640

Ala Leu Ala Asp Gly Glu His Phe Ile Val Asp Pro Asp Lys Leu Ser
                645                 650                 655

Ser Thr Ile Val Asp Leu Glu Lys Ile Leu Lys Leu Ile Glu Gly Leu
            660                 665                 670

Asp Tyr Ser Thr Leu Arg Gln Thr Thr Gln Thr Gln Phe Arg Asp Met
        675                 680                 685

Thr Thr Ala Gly Lys Ala Leu Leu Ser Lys Ser Asn Leu Arg Gln Gly
    690                 695                 700

Glu Lys Gln Lys Phe Leu Gln Glu Ala Gln Phe Phe Leu Gly Arg Val
705                 710                 715                 720

Asp Leu Asp Lys Ala Ile Ala Lys Ala Glu Lys Ala Leu Val Thr Lys
                725                 730                 735

Lys Ala Thr Lys Asn Gly Gln Leu Leu Glu Arg Ser Ile Asn Lys Ala
            740                 745                 750

Val Leu Ala Tyr Asn Asn Ser Ala Ile Lys Lys Ala Asn Val Lys Arg
        755                 760                 765

Leu Glu Lys Glu Leu Asp Leu Leu Thr Gly Leu Val Glu Gly Lys Gly
    770                 775                 780
```

-continued

Pro Leu Ala Gln Ala Thr Met Val Gln Gly Val Tyr Leu Leu Lys Thr
785                 790                 795                 800

Pro Leu Pro Leu Pro Glu Tyr Tyr Ile Gly Leu Asn Val Tyr Phe Asp
            805                 810                 815

Lys Ser Gly Lys Leu Ile Tyr Ala Leu Asp Met Ser Asp Thr Ile Gly
        820                 825                 830

Glu Gly Gln Lys Asp Ala Tyr Gly Asn Pro Ile Leu Asn Val Asp Glu
    835                 840                 845

Asp Asn Glu Gly Tyr His Ala Leu Ala Val Ala Thr Leu Ala Asp Tyr
850                 855                 860

Glu Gly Leu Asp Ile Lys Thr Ile Leu Asn Ser Lys Leu Ser Gln Leu
865                 870                 875                 880

Thr Ser Ile Arg Gln Val Pro Thr Ala Ala Tyr His Arg Ala Gly Ile
                885                 890                 895

Phe Gln Ala Ile Gln Asn Ala Ala Ala Glu Ala Glu Gln Leu Leu Pro
            900                 905                 910

Lys Ala Gly Thr His Ser Glu Lys Ser Ser Ser Glu Ser Ala Asn
        915                 920                 925

Ser Lys Asp Arg Gly Leu Gln Ser Asn Pro Lys Thr Asn Arg Gly Arg
    930                 935                 940

His Ser Ala Ile Leu Pro Arg Thr Gly Ser Lys Gly Ser Phe Val Tyr
945                 950                 955                 960

Gly Ile Leu Gly Tyr Thr Ser Val Ala Leu
                965                 970

<210> SEQ ID NO 5
<211> LENGTH: 963
<212> TYPE: PRT
<213> ORGANISM: Streptococcus pyogenes

<400> SEQUENCE: 5

Lys Gln Thr Gln Ala Ser Ser Ile Ser Gly Ala Asp Tyr Ala Glu
1               5                   10                  15

Ser Ser Gly Lys Ser Lys Leu Lys Ile Asn Glu Thr Ser Gly Pro Val
            20                  25                  30

Asp Asp Thr Val Thr Asp Leu Phe Ser Asp Lys Arg Thr Thr Pro Glu
        35                  40                  45

Lys Ile Lys Asp Asn Leu Ala Lys Gly Pro Arg Glu Gln Glu Leu Lys
    50                  55                  60

Ala Val Thr Glu Asn Thr Glu Ser Glu Lys Gln Ile Asn Ser Gly Ser
65                  70                  75                  80

Gln Leu Glu Gln Ser Lys Glu Ser Leu Ser Leu Asn Lys Arg Val Pro
                85                  90                  95

Ser Thr Ser Asn Trp Glu Ile Cys Asp Phe Ile Thr Lys Gly Asn Thr
            100                 105                 110

Leu Val Gly Leu Ser Lys Ser Gly Val Glu Lys Leu Ser Gln Thr Asp
        115                 120                 125

His Leu Val Leu Pro Ser Gln Ala Ala Asp Gly Thr Gln Leu Ile Gln
    130                 135                 140

Val Ala Ser Phe Ala Phe Thr Pro Asp Lys Lys Thr Ala Ile Ala Glu
145                 150                 155                 160

Tyr Thr Ser Arg Ala Gly Glu Asn Gly Glu Ile Ser Gln Leu Asp Val
                165                 170                 175

Asp Gly Lys Glu Ile Ile Asn Glu Gly Glu Val Phe Asn Ser Tyr Leu
            180                 185                 190

-continued

```
Leu Lys Lys Val Thr Ile Pro Thr Gly Tyr Lys His Ile Gly Gln Asp
            195                 200                 205
Ala Phe Val Asp Asn Lys Asn Ile Ala Glu Val Asn Leu Pro Glu Ser
        210                 215                 220
Leu Glu Thr Ile Ser Asp Tyr Ala Phe Ala His Leu Ala Leu Lys Gln
225                 230                 235                 240
Ile Asp Leu Pro Asp Asn Leu Lys Ala Ile Gly Glu Leu Ala Phe Phe
                245                 250                 255
Asp Asn Gln Ile Thr Gly Lys Leu Ser Leu Pro Arg Gln Leu Met Arg
            260                 265                 270
Leu Ala Glu Arg Ala Phe Lys Ser Asn His Ile Lys Thr Ile Glu Phe
        275                 280                 285
Arg Gly Asn Ser Leu Lys Val Ile Gly Glu Ala Ser Phe Gln Asp Asn
        290                 295                 300
Asp Leu Ser Gln Leu Met Leu Pro Asp Gly Leu Glu Lys Ile Glu Ser
305                 310                 315                 320
Glu Ala Phe Thr Gly Asn Pro Gly Asp His Tyr Asn Asn Arg Val
                325                 330                 335
Val Leu Trp Thr Lys Ser Gly Lys Asn Pro Tyr Gly Leu Ala Thr Glu
            340                 345                 350
Asn Thr Tyr Val Asn Pro Asp Lys Ser Leu Trp Gln Glu Ser Pro Glu
        355                 360                 365
Ile Asp Tyr Thr Lys Trp Leu Glu Glu Asp Phe Thr Tyr Gln Lys Asn
    370                 375                 380
Ser Val Thr Gly Phe Ser Ser Lys Gly Leu Gln Lys Val Lys Arg Asn
385                 390                 395                 400
Lys Asn Leu Glu Ile Pro Lys Gln His Asn Gly Val Thr Ile Thr Glu
                405                 410                 415
Ile Gly Asp Asn Ala Phe Arg Asn Val Asn Phe Gln Asn Lys Thr Leu
            420                 425                 430
Arg Lys Tyr Asp Leu Glu Glu Val Lys Leu Pro Ser Thr Ile Arg Lys
        435                 440                 445
Ile Gly Ala Phe Ala Phe Gln Ser Asn Asn Leu Lys Ser Phe Glu Ala
    450                 455                 460
Ser Asp Asp Leu Glu Glu Ile Lys Glu Gly Ala Phe Met Asn Asn Arg
465                 470                 475                 480
Ile Glu Thr Leu Glu Leu Lys Asp Lys Leu Val Thr Ile Gly Asp Ala
                485                 490                 495
Ala Phe His Ile Asn His Ile Tyr Ala Ile Val Leu Pro Glu Ser Val
            500                 505                 510
Gln Glu Ile Gly Arg Ser Ala Phe Arg Gln Asn Gly Ala Asn Asn Leu
        515                 520                 525
Ile Phe Met Gly Ser Lys Val Lys Thr Leu Gly Glu Met Ala Phe Leu
    530                 535                 540
Ser Asn Arg Leu Glu His Leu Asp Leu Ser Glu Gln Lys Gln Leu Thr
545                 550                 555                 560
Glu Ile Pro Val Gln Ala Phe Ser Asp Asn Ala Leu Lys Glu Val Leu
                565                 570                 575
Leu Pro Ala Ser Leu Lys Thr Ile Arg Glu Glu Ala Phe Lys Lys Asn
            580                 585                 590
His Leu Lys Gln Leu Glu Val Ala Ser Ala Leu Ser His Ile Ala Phe
        595                 600                 605
```

```
Asn Ala Leu Asp Asp Asn Asp Gly Asp Glu Gln Phe Asp Asn Lys Val
        610                 615                 620

Val Val Lys Thr His His Asn Ser Tyr Ala Leu Ala Asp Gly Glu His
625                 630                 635                 640

Phe Ile Val Asp Pro Asp Lys Leu Ser Ser Thr Ile Val Asp Leu Glu
                645                 650                 655

Lys Ile Leu Lys Leu Ile Glu Gly Leu Asp Tyr Ser Thr Leu Arg Gln
                660                 665                 670

Thr Thr Gln Thr Gln Phe Arg Asp Met Thr Thr Ala Gly Lys Ala Leu
            675                 680                 685

Leu Ser Lys Ser Asn Leu Arg Gln Gly Glu Lys Gln Lys Phe Leu Gln
690                 695                 700

Glu Ala Gln Phe Phe Leu Gly Arg Val Asp Leu Asp Lys Ala Ile Ala
705                 710                 715                 720

Lys Ala Glu Lys Ala Leu Val Thr Lys Ala Thr Lys Asn Gly Gln
                725                 730                 735

Leu Leu Glu Arg Ser Ile Asn Lys Ala Val Ser Ala Tyr Asn Asn Ser
                740                 745                 750

Ala Ile Lys Lys Ala Asn Val Lys Arg Leu Glu Lys Glu Leu Asp Leu
                755                 760                 765

Leu Thr Gly Leu Val Glu Gly Lys Gly Pro Leu Ala Gln Ala Thr Met
770                 775                 780

Val Gln Gly Val Tyr Leu Leu Lys Thr Pro Leu Pro Leu Pro Glu Tyr
785                 790                 795                 800

Tyr Ile Gly Leu Asn Val Tyr Phe Asp Lys Ser Gly Lys Leu Ile Tyr
                805                 810                 815

Ala Leu Asp Met Ser Asp Thr Ile Gly Glu Gly Gln Lys Asp Ala Tyr
                820                 825                 830

Gly Asn Pro Ile Leu Asn Val Asp Glu Asp Asn Glu Gly Tyr His Ala
                835                 840                 845

Leu Ala Val Ala Thr Leu Ala Asp Tyr Glu Gly Leu Asp Ile Lys Thr
850                 855                 860

Ile Leu Asn Ser Lys Leu Ser Gln Leu Thr Ser Ile Arg Gln Val Pro
865                 870                 875                 880

Thr Ala Ala Tyr His Arg Ala Gly Ile Phe Gln Ala Ile Gln Asn Ala
                885                 890                 895

Ala Ala Glu Ala Glu Gln Leu Leu Pro Lys Pro Gly Thr His Ser Glu
                900                 905                 910

Lys Ser Ser Ser Glu Ser Ala Asn Ser Lys Asp Arg Gly Leu Gln
                915                 920                 925

Ser Asn Pro Lys Thr Asn Arg Gly Arg His Ser Ala Ile Leu Pro Arg
930                 935                 940

Thr Gly Ser Lys Gly Ser Phe Val Tyr Gly Ile Leu Gly Tyr Thr Ser
945                 950                 955                 960

Val Ala Leu

<210> SEQ ID NO 6
<211> LENGTH: 971
<212> TYPE: PRT
<213> ORGANISM: Streptococcus pyogenes

<400> SEQUENCE: 6

Leu Val Lys Glu Pro Ile Leu Lys Gln Thr Gln Ala Ser Ser Ser Ile
 1               5                  10                  15
```

-continued

```
Ser Gly Ala Asp Tyr Ala Glu Ser Ser Gly Lys Ser Lys Leu Lys Ile
            20                  25                  30

Asn Glu Thr Ser Gly Pro Val Asp Thr Val Thr Asp Leu Phe Ser
        35                  40                  45

Asp Lys Arg Thr Thr Pro Glu Lys Ile Lys Asp Asn Leu Ala Lys Gly
 50                  55                  60

Pro Arg Glu Gln Glu Leu Lys Thr Val Thr Glu Asn Thr Glu Ser Glu
 65                  70                  75                  80

Lys Gln Ile Thr Ser Gly Ser Gln Leu Glu Gln Ser Lys Glu Ser Leu
                85                  90                  95

Ser Leu Asn Lys Thr Val Pro Ser Thr Ser Asn Trp Glu Ile Cys Asp
            100                 105                 110

Phe Ile Thr Lys Gly Asn Thr Leu Val Gly Leu Ser Lys Ser Gly Val
            115                 120                 125

Glu Lys Leu Ser Gln Thr Asp His Leu Val Leu Pro Ser Gln Ala Ala
130                 135                 140

Asp Gly Thr Gln Leu Ile Gln Val Ala Ser Phe Ala Phe Thr Pro Asp
145                 150                 155                 160

Lys Lys Thr Ala Ile Ala Glu Tyr Thr Ser Arg Ala Gly Glu Asn Gly
                165                 170                 175

Glu Ile Ser Gln Leu Asp Val Asp Gly Lys Glu Ile Ile Asn Glu Gly
            180                 185                 190

Glu Val Phe Asn Ser Tyr Leu Leu Lys Lys Val Thr Ile Pro Thr Gly
            195                 200                 205

Tyr Lys His Ile Gly Gln Asp Ala Phe Val Asp Asn Lys Asn Ile Ala
 210                 215                 220

Glu Val Asn Leu Pro Glu Ser Leu Glu Thr Ile Ser Asp Tyr Ala Phe
225                 230                 235                 240

Ala His Leu Ala Leu Lys Gln Ile Asp Leu Pro Asp Asn Leu Lys Ala
                245                 250                 255

Ile Gly Glu Leu Ala Phe Phe Asp Asn Gln Ile Thr Gly Lys Leu Ser
            260                 265                 270

Leu Pro Arg Gln Leu Met Arg Leu Ala Glu Arg Ala Phe Lys Ser Asn
            275                 280                 285

His Ile Lys Thr Ile Glu Phe Arg Gly Asn Ser Leu Lys Val Ile Gly
        290                 295                 300

Glu Ala Ser Phe Gln Asp Asn Asp Leu Ser Gln Leu Met Leu Pro Asp
305                 310                 315                 320

Gly Leu Glu Lys Ile Glu Ser Glu Ala Phe Thr Gly Asn Pro Gly Asp
                325                 330                 335

Asp His Tyr Asn Asn Arg Val Val Leu Trp Thr Lys Ser Gly Lys Asn
            340                 345                 350

Pro Tyr Gly Leu Ala Thr Glu Asn Thr Tyr Val Asn Pro Asp Lys Ser
        355                 360                 365

Leu Trp Gln Glu Ser Pro Glu Ile Asp Tyr Thr Lys Trp Leu Glu Glu
 370                 375                 380

Asp Phe Thr Tyr Gln Lys Asn Ser Val Thr Gly Phe Ser Asn Lys Gly
385                 390                 395                 400

Leu Gln Lys Val Lys Arg Asn Lys Asn Leu Glu Ile Pro Lys Gln His
                405                 410                 415

Asn Gly Val Thr Ile Thr Glu Ile Gly Asp Asn Ala Phe Arg Asn Val
            420                 425                 430

Asp Phe Gln Asn Lys Thr Leu Arg Lys Tyr Asp Leu Glu Glu Val Lys
```

```
                435                 440                 445
Leu Pro Ser Thr Ile Arg Lys Ile Gly Ala Phe Ala Phe Gln Ser Asn
        450                 455                 460

Asn Leu Lys Ser Phe Glu Ala Ser Asp Asp Leu Glu Glu Ile Lys Glu
465                 470                 475                 480

Gly Ala Phe Met Asn Asn Arg Ile Glu Thr Leu Glu Leu Lys Asp Lys
                485                 490                 495

Leu Val Thr Ile Gly Asp Ala Ala Phe His Ile Asn His Ile Tyr Ala
            500                 505                 510

Ile Val Leu Pro Glu Ser Val Gln Glu Ile Gly Arg Ser Ala Phe Arg
                515                 520                 525

Gln Asn Gly Ala Asn Asn Leu Ile Phe Met Gly Ser Lys Val Lys Thr
        530                 535                 540

Leu Gly Glu Met Ala Phe Leu Ser Asn Arg Leu Glu His Leu Asp Leu
545                 550                 555                 560

Ser Glu Gln Lys Gln Leu Thr Glu Ile Pro Val Gln Ala Phe Ser Asp
                565                 570                 575

Asn Ala Leu Lys Glu Val Leu Leu Pro Ala Ser Leu Lys Thr Ile Arg
        580                 585                 590

Glu Glu Ala Phe Lys Lys Asn His Leu Lys Gln Leu Glu Val Ala Ser
595                 600                 605

Ala Leu Ser His Ile Ala Phe Asn Ala Leu Asp Asp Asn Asp Gly Asp
        610                 615                 620

Glu Gln Phe Asp Asn Lys Val Val Lys Thr His His Asn Ser Tyr
625                 630                 635                 640

Ala Leu Ala Asp Gly Glu His Phe Ile Val Asp Pro Asp Lys Leu Ser
                645                 650                 655

Ser Thr Met Ile Asp Leu Glu Lys Ile Leu Lys Leu Ile Glu Gly Leu
        660                 665                 670

Asp Tyr Ser Thr Leu Arg Gln Thr Thr Gln Thr Gln Phe Arg Asp Met
                675                 680                 685

Thr Thr Ala Gly Lys Ala Leu Leu Ser Lys Ser Asn Leu Arg Gln Gly
690                 695                 700

Glu Lys Gln Lys Phe Leu Gln Glu Ala Gln Phe Phe Leu Gly Arg Val
705                 710                 715                 720

Asp Leu Asp Lys Ala Ile Ala Lys Ala Glu Lys Ala Leu Val Thr Lys
                725                 730                 735

Lys Ala Thr Lys Asn Gly Gln Leu Leu Glu Arg Ser Ile Asn Lys Ala
        740                 745                 750

Val Leu Ala Tyr Asn Asn Ser Ala Ile Lys Lys Ala Asn Val Lys Arg
        755                 760                 765

Leu Glu Lys Glu Leu Asp Leu Leu Thr Gly Leu Val Glu Gly Lys Gly
        770                 775                 780

Pro Leu Ala Gln Ala Thr Met Val Gln Gly Val Tyr Leu Leu Lys Thr
785                 790                 795                 800

Pro Leu Pro Leu Pro Glu Tyr Tyr Ile Gly Leu Asn Val Tyr Phe Asp
                805                 810                 815

Lys Ser Gly Lys Leu Ile Tyr Ala Leu Asp Met Ser Asp Thr Ile Gly
                820                 825                 830

Glu Gly Gln Lys Asp Ala Tyr Gly Asn Pro Ile Leu Asn Val Asp Glu
        835                 840                 845

Asp Asn Glu Gly Tyr His Ala Leu Ala Val Ala Thr Leu Ala Asp Tyr
850                 855                 860
```

```
Glu Gly Leu Asp Ile Lys Thr Ile Leu Asn Ser Lys Leu Ser Gln Leu
865                 870                 875                 880

Thr Ser Ile Arg Gln Val Pro Thr Ala Ala Tyr His Arg Ala Gly Ile
            885                 890                 895

Phe Gln Ala Ile Gln Asn Ala Ala Ala Glu Ala Glu Gln Leu Leu Pro
            900                 905                 910

Lys Pro Gly Met His Ser Glu Lys Ser Ser Ser Glu Ser Ala Asn
            915                 920                 925

Ser Lys Asp Arg Gly Leu Gln Ser His Pro Lys Thr Asn Arg Gly Arg
930                 935                 940

His Ser Ala Ile Leu Pro Arg Thr Gly Ser Lys Gly Ser Phe Val Tyr
945                 950                 955                 960

Gly Ile Leu Gly Tyr Thr Ser Val Ala Leu Leu
                965                 970

<210> SEQ ID NO 7
<211> LENGTH: 971
<212> TYPE: PRT
<213> ORGANISM: Streptococcus pyogenes

<400> SEQUENCE: 7

Leu Val Lys Glu Pro Ile Leu Lys Gln Thr Gln Ala Ser Ser Ser Ile
1               5                   10                  15

Ser Gly Ala Asp Tyr Ala Glu Ser Ser Gly Lys Ser Lys Leu Lys Ile
            20                  25                  30

Asn Glu Thr Ser Gly Pro Val Asp Asp Thr Val Thr Asp Leu Phe Ser
        35                  40                  45

Asp Lys Arg Thr Thr Pro Glu Lys Ile Lys Asp Asn Leu Ala Lys Gly
    50                  55                  60

Pro Arg Glu Gln Glu Leu Lys Ala Val Thr Glu Asn Thr Glu Ser Glu
65                  70                  75                  80

Lys Gln Ile Thr Ser Gly Ser Gln Leu Glu Gln Ser Lys Glu Ser Leu
                85                  90                  95

Ser Leu Asn Lys Thr Val Pro Ser Thr Ser Asn Trp Glu Ile Cys Asp
            100                 105                 110

Phe Ile Thr Lys Gly Asn Thr Leu Val Gly Leu Ser Lys Ser Gly Val
        115                 120                 125

Glu Lys Leu Ser Gln Thr Asp His Leu Val Leu Pro Ser Gln Ala Ala
130                 135                 140

Asp Gly Thr Gln Leu Ile Gln Val Ala Ser Phe Ala Phe Thr Pro Asp
145                 150                 155                 160

Lys Lys Thr Ala Ile Ala Glu Tyr Thr Ser Arg Ala Gly Glu Asn Gly
                165                 170                 175

Glu Ile Ser Gln Leu Asp Val Asp Gly Lys Glu Ile Ile Asn Glu Gly
            180                 185                 190

Glu Val Phe Asn Ser Tyr Leu Leu Lys Lys Val Thr Ile Pro Thr Gly
        195                 200                 205

Tyr Lys His Ile Gly Gln Asp Ala Phe Val Asp Asn Lys Asn Ile Ala
    210                 215                 220

Glu Val Asn Leu Pro Glu Ser Leu Glu Thr Ile Ser Asp Tyr Ala Phe
225                 230                 235                 240

Ala His Leu Ala Leu Lys Gln Ile Asp Leu Pro Asp Asn Leu Lys Ala
                245                 250                 255

Ile Gly Glu Leu Ala Phe Phe Asp Asn Gln Ile Thr Gly Lys Leu Ser
```

-continued

```
                260                 265                 270
Leu Pro Arg Gln Leu Met Arg Leu Ala Glu Arg Ala Phe Lys Ser Asn
                275                 280                 285
His Ile Lys Thr Ile Glu Phe Arg Gly Asn Ser Leu Lys Val Ile Gly
            290                 295                 300
Glu Ala Ser Phe Gln Asp Asn Asp Leu Ser Gln Leu Met Leu Pro Asp
305                 310                 315                 320
Gly Leu Glu Lys Ile Glu Ser Glu Ala Phe Thr Gly Asn Pro Gly Asp
                325                 330                 335
Asp His Tyr Asn Asn Arg Val Val Leu Trp Thr Lys Ser Gly Lys Asn
            340                 345                 350
Pro Ser Gly Leu Ala Thr Glu Asn Thr Tyr Val Asn Pro Asp Lys Ser
        355                 360                 365
Leu Trp Gln Glu Ser Pro Glu Ile Asp Tyr Thr Lys Trp Leu Glu Glu
    370                 375                 380
Asp Phe Thr Tyr Gln Lys Asn Ser Val Thr Gly Phe Ser Asn Lys Gly
385                 390                 395                 400
Leu Gln Lys Val Lys Arg Asn Lys Asn Leu Glu Ile Pro Lys Gln His
                405                 410                 415
Asn Gly Val Thr Ile Thr Glu Ile Gly Asp Asn Ala Phe Arg Asn Val
            420                 425                 430
Asp Phe Gln Asn Lys Thr Leu Arg Lys Tyr Asp Leu Glu Glu Val Lys
        435                 440                 445
Leu Pro Ser Thr Ile Arg Lys Ile Gly Ala Phe Ala Phe Gln Ser Asn
    450                 455                 460
Asn Leu Lys Ser Phe Glu Ala Ser Asp Asp Leu Glu Glu Ile Lys Glu
465                 470                 475                 480
Gly Ala Phe Met Asn Asn Arg Ile Glu Thr Leu Glu Leu Lys Asp Lys
                485                 490                 495
Leu Val Thr Ile Gly Asp Ala Ala Phe His Ile Asn His Ile Tyr Ala
            500                 505                 510
Ile Val Leu Pro Glu Ser Val Gln Glu Ile Gly Arg Ser Ala Phe Arg
        515                 520                 525
Gln Asn Gly Ala Asn Asn Leu Ile Phe Met Gly Ser Lys Val Lys Thr
    530                 535                 540
Leu Gly Glu Met Ala Phe Leu Ser Asn Arg Leu Glu His Leu Asp Leu
545                 550                 555                 560
Ser Glu Gln Lys Gln Leu Thr Glu Ile Pro Val Gln Ala Phe Ser Asp
                565                 570                 575
Asn Ala Leu Lys Glu Val Leu Leu Pro Ala Ser Leu Lys Thr Ile Arg
            580                 585                 590
Glu Glu Ala Phe Lys Lys Asn His Leu Lys Gln Leu Glu Val Ala Ser
        595                 600                 605
Ala Leu Ser His Ile Ala Phe Asn Ala Leu Asp Asp Asn Asp Gly Asp
    610                 615                 620
Glu Gln Phe Asp Asn Lys Val Val Lys Thr His His Asn Ser Tyr
625                 630                 635                 640
Ala Leu Ala Asp Gly Glu His Phe Ile Val Asp Pro Asp Lys Leu Ser
                645                 650                 655
Ser Thr Ile Val Asp Leu Glu Lys Ile Leu Lys Leu Ile Glu Gly Leu
            660                 665                 670
Asp Tyr Ser Thr Leu Arg Gln Thr Gln Thr Gln Phe Arg Asp Met
        675                 680                 685
```

```
Thr Thr Ala Gly Lys Ala Leu Leu Ser Lys Ser Asn Leu Arg Gln Gly
    690             695                 700

Glu Lys Gln Lys Phe Leu Gln Glu Ala Gln Phe Phe Leu Gly Arg Val
705             710                 715                 720

Asp Leu Asp Lys Ala Ile Ala Lys Ala Glu Lys Ala Leu Val Thr Lys
                725                 730                 735

Lys Ala Thr Lys Asn Gly Gln Leu Leu Glu Arg Ser Ile Asn Lys Ala
            740                 745                 750

Val Leu Ala Tyr Asn Asn Ser Ala Ile Lys Lys Ala Asn Val Lys Arg
        755                 760                 765

Leu Glu Lys Glu Leu Asp Leu Leu Thr Gly Leu Val Glu Gly Lys Gly
    770                 775                 780

Pro Leu Ala Gln Ala Thr Met Val Gln Gly Val Tyr Leu Leu Lys Thr
785                 790                 795                 800

Pro Leu Pro Leu Pro Glu Tyr Tyr Ile Gly Leu Asn Val Tyr Phe Asp
                805                 810                 815

Lys Ser Gly Lys Leu Ile Tyr Ala Leu Asp Met Ser Asp Thr Ile Gly
            820                 825                 830

Glu Gly Gln Lys Asp Ala Tyr Gly Asn Pro Ile Leu Asn Val Asp Glu
        835                 840                 845

Asp Asn Glu Gly Tyr His Ala Leu Ala Val Ala Thr Leu Ala Asp Tyr
    850                 855                 860

Glu Gly Leu Asp Ile Lys Thr Ile Leu Asn Ser Lys Leu Ser Gln Leu
865                 870                 875                 880

Thr Ser Ile Arg Gln Val Pro Thr Ala Ala Tyr His Arg Ala Gly Ile
                885                 890                 895

Phe Gln Ala Ile Gln Asn Ala Ala Glu Ala Glu Gln Leu Leu Pro
            900                 905                 910

Lys Pro Gly Thr His Ser Glu Lys Ser Ser Ser Glu Ser Ala Asn
        915                 920                 925

Ser Lys Asp Arg Gly Leu Gln Ser Asn Pro Lys Thr Asn Arg Gly Arg
930                 935                 940

His Ser Ala Ile Leu Pro Arg Thr Gly Ser Lys Gly Ser Phe Val Tyr
945                 950                 955                 960

Gly Ile Leu Gly Tyr Thr Ser Val Ala Leu Leu
                965                 970

<210> SEQ ID NO 8
<211> LENGTH: 969
<212> TYPE: PRT
<213> ORGANISM: Streptococcus pyogenes

<400> SEQUENCE: 8

Val Lys Glu Pro Ile Leu Lys Gln Thr Gln Ala Ser Ser Ser Ile Ser
  1               5                  10                  15

Gly Ala Asp Tyr Ala Glu Ser Ser Gly Lys Ser Lys Leu Lys Ile Asn
                20                  25                  30

Glu Thr Ser Gly Pro Val Asp Asp Thr Val Thr Asp Leu Phe Ser Asp
            35                  40                  45

Lys Arg Thr Thr Pro Glu Lys Ile Lys Asp Asn Leu Ala Lys Gly Pro
        50                  55                  60

Arg Glu Gln Glu Leu Lys Ala Val Thr Glu Asn Thr Glu Ser Glu Lys
65                  70                  75                  80

Gln Ile Asn Ser Gly Ser Gln Leu Glu Gln Ser Lys Glu Ser Leu Ser
```

```
                 85                  90                  95
Leu Asn Lys Arg Val Pro Ser Thr Ser Asn Trp Glu Ile Cys Asp Phe
            100                 105                 110
Ile Thr Lys Gly Asn Thr Leu Val Gly Leu Ser Lys Ser Gly Val Glu
            115                 120                 125
Lys Leu Ser Gln Thr Asp His Leu Val Leu Pro Ser Gln Ala Ala Asp
            130                 135                 140
Gly Thr Gln Leu Ile Gln Val Ala Ser Phe Ala Phe Thr Pro Asp Lys
145                 150                 155                 160
Lys Thr Ala Ile Ala Glu Tyr Thr Ser Arg Ala Gly Glu Asn Gly Glu
                165                 170                 175
Ile Ser Gln Leu Asp Val Asp Gly Lys Glu Ile Ile Asn Glu Gly Glu
            180                 185                 190
Val Phe Asn Ser Tyr Leu Leu Lys Lys Val Thr Ile Pro Thr Gly Tyr
            195                 200                 205
Lys His Ile Gly Gln Asp Ala Phe Val Asp Asn Lys Asn Ile Ala Glu
            210                 215                 220
Val Asn Leu Pro Glu Ser Leu Glu Thr Ile Ser Asp Tyr Ala Phe Ala
225                 230                 235                 240
His Leu Ala Leu Lys Gln Ile Asp Leu Pro Asp Asn Leu Lys Ala Ile
                245                 250                 255
Gly Glu Leu Ala Phe Phe Asp Asn Gln Ile Thr Gly Lys Leu Ser Leu
            260                 265                 270
Pro Arg Gln Leu Met Arg Leu Ala Glu Arg Ala Phe Lys Ser Asn His
            275                 280                 285
Ile Lys Thr Ile Glu Phe Arg Gly Asn Ser Leu Lys Val Ile Gly Glu
            290                 295                 300
Ala Ser Phe Gln Asp Asn Asp Leu Ser Gln Leu Met Leu Pro Asp Gly
305                 310                 315                 320
Leu Glu Lys Ile Glu Ser Glu Ala Phe Thr Gly Asn Pro Gly Asp Asp
                325                 330                 335
His Tyr Asn Asn Arg Val Val Leu Trp Thr Lys Ser Gly Lys Asn Pro
            340                 345                 350
Tyr Gly Leu Ala Thr Glu Asn Thr Tyr Val Asn Pro Asp Lys Ser Leu
            355                 360                 365
Trp Gln Glu Ser Pro Glu Ile Asp Tyr Thr Lys Trp Leu Glu Glu Asp
            370                 375                 380
Phe Thr Tyr Gln Lys Asn Ser Val Thr Gly Phe Ser Ser Lys Gly Leu
385                 390                 395                 400
Gln Lys Val Lys Arg Asn Lys Asn Leu Glu Ile Pro Lys Gln His Asn
                405                 410                 415
Gly Val Thr Ile Thr Glu Ile Gly Asp Asn Ala Phe Arg Asn Val Asp
            420                 425                 430
Phe Gln Asn Lys Thr Leu Arg Lys Tyr Asp Leu Glu Glu Val Lys Leu
            435                 440                 445
Pro Ser Thr Ile Arg Lys Ile Gly Ala Phe Ala Phe Gln Ser Asn Asn
450                 455                 460
Leu Lys Ser Phe Glu Ala Ser Asp Asp Leu Glu Glu Ile Lys Glu Gly
465                 470                 475                 480
Ala Phe Met Asn Asn Arg Ile Glu Thr Leu Glu Leu Lys Asp Lys Leu
                485                 490                 495
Val Thr Ile Gly Asp Ala Ala Phe His Ile Asn His Ile Tyr Ala Ile
            500                 505                 510
```

```
Val Leu Pro Glu Ser Val Gln Glu Ile Gly Arg Ser Ala Phe Arg Gln
            515                 520                 525

Asn Gly Ala Asn Asn Leu Ile Phe Met Gly Ser Lys Val Lys Thr Leu
        530                 535                 540

Gly Glu Met Ala Phe Leu Ser Asn Arg Leu Glu His Leu Asp Leu Ser
545                 550                 555                 560

Glu Gln Lys Gln Leu Thr Glu Ile Pro Val Gln Ala Phe Ser Asp Asn
                565                 570                 575

Ala Leu Lys Glu Val Leu Leu Pro Ala Ser Leu Lys Thr Ile Arg Glu
            580                 585                 590

Glu Ala Phe Lys Lys Asn His Leu Lys Gln Leu Glu Val Ala Ser Ala
        595                 600                 605

Leu Ser His Ile Ala Phe Asn Ala Leu Asp Asp Asn Gly Asp Glu
610                 615                 620

Gln Phe Asp Asn Lys Val Val Lys Thr His His Asn Ser Tyr Ala
625                 630                 635                 640

Leu Ala Asp Gly Glu His Phe Ile Val Asp Pro Asp Lys Leu Ser Ser
            645                 650                 655

Thr Ile Val Asp Leu Glu Lys Ile Leu Lys Leu Ile Glu Gly Leu Asp
                660                 665                 670

Tyr Ser Thr Leu Arg Gln Thr Thr Gln Thr Gln Phe Arg Asp Met Thr
            675                 680                 685

Thr Ala Gly Lys Ala Leu Leu Ser Lys Ser Asn Leu Arg Gln Gly Glu
690                 695                 700

Lys Gln Lys Phe Leu Gln Glu Ala Gln Phe Phe Leu Gly Arg Val Asp
705                 710                 715                 720

Leu Asp Lys Ala Ile Ala Lys Ala Glu Lys Ala Leu Val Thr Lys Lys
                725                 730                 735

Ala Thr Lys Asn Gly Gln Leu Leu Glu Arg Ser Ile Asn Lys Ala Val
            740                 745                 750

Leu Ala Tyr Asn Asn Ser Ala Ile Lys Lys Ala Asn Val Lys Arg Leu
        755                 760                 765

Glu Lys Glu Leu Asp Leu Leu Thr Gly Leu Val Glu Gly Lys Gly Pro
    770                 775                 780

Leu Ala Gln Ala Thr Met Val Gln Gly Val Tyr Leu Leu Lys Thr Pro
785                 790                 795                 800

Leu Pro Leu Pro Glu Tyr Tyr Ile Gly Leu Asn Val Tyr Phe Asp Lys
                805                 810                 815

Ser Gly Lys Leu Ile Tyr Ala Leu Asp Met Ser Asp Thr Ile Gly Glu
            820                 825                 830

Gly Gln Lys Asp Ala Tyr Gly Asn Pro Ile Leu Asn Val Asp Glu Asp
        835                 840                 845

Asn Glu Gly Tyr His Ala Leu Ala Val Ala Thr Leu Ala Asp Tyr Glu
    850                 855                 860

Gly Leu Asp Ile Lys Thr Ile Leu Asn Ser Lys Leu Ser Gln Leu Thr
865                 870                 875                 880

Ser Ile Arg Gln Val Pro Thr Ala Ala Tyr His Arg Ala Gly Ile Phe
                885                 890                 895

Gln Ala Ile Gln Asn Ala Ala Ala Glu Ala Gln Leu Leu Pro Lys
            900                 905                 910

Pro Gly Thr His Ser Glu Lys Ser Ser Ser Glu Ser Ala Asn Ser
        915                 920                 925
```

-continued

```
Lys Asp Arg Gly Leu Gln Ser Asn Pro Lys Thr Asn Arg Gly Arg His
        930                 935                 940

Ser Ala Ile Leu Pro Arg Thr Gly Ser Lys Gly Ser Phe Val Tyr Gly
945                 950                 955                 960

Ile Leu Gly Tyr Thr Ser Val Ala Leu
            965

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 9
gtagtcaccc accatatgga agttttag                                      29

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 10
tttttctttt gcggccgcag ttattagt                                      28

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 11
ggggatccca cccacaatca gg                                            22

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 12
ggttgtcgac agtaaagcaa cgctagtg                                      28

<210> SEQ ID NO 13
<211> LENGTH: 21
<212> TYPE: PRT
<213> ORGANISM: Unknown Organism
<220> FEATURE:
<223> OTHER INFORMATION: Description of Unknown Organism: Signal peptide

<400> SEQUENCE: 13

Met Lys Lys His Leu Lys Thr Val Ala Leu Thr Leu Thr Thr Val Ser
 1               5                  10                  15

Val Val Thr His Asn
            20

<210> SEQ ID NO 14
<211> LENGTH: 6
<212> TYPE: PRT
<213> ORGANISM: Unknown Organism
<220> FEATURE:
```

```
<223> OTHER INFORMATION: Description of Unknown Organism: Anchoring
      motif
<220> FEATURE:
<221> NAME/KEY: MOD_RES
<222> LOCATION: (3)
<223> OTHER INFORMATION: Any amino acid
<220> FEATURE:
<221> NAME/KEY: MOD_RES
<222> LOCATION: (6)
<223> OTHER INFORMATION: Any amino acid

<400> SEQUENCE: 14

Leu Pro Xaa Thr Gly Xaa
 1               5
```